(12) United States Patent
Low

(10) Patent No.: US 12,211,603 B2
(45) Date of Patent: Jan. 28, 2025

(54) AUTHENTICATION METHODS AND SYSTEMS FOR DISPENSED PRESCRIPTIONS

(71) Applicant: Gordon Keith Low, Salt Lake City, UT (US)

(72) Inventor: Gordon Keith Low, Salt Lake City, UT (US)

(*) Notice: Subject to any disclaimer, the term of this patent is extended or adjusted under 35 U.S.C. 154(b) by 0 days.

(21) Appl. No.: 18/444,865

(22) Filed: Feb. 19, 2024

(65) Prior Publication Data

US 2024/0282425 A1    Aug. 22, 2024

Related U.S. Application Data

(60) Provisional application No. 63/446,812, filed on Feb. 18, 2023.

(51) Int. Cl.

| | |
|---|---|
| *G16H 20/13* | (2018.01) |
| *G06K 7/14* | (2006.01) |
| *G06K 19/06* | (2006.01) |
| *G06K 19/07* | (2006.01) |
| *G06Q 50/00* | (2012.01) |
| *G16H 10/60* | (2018.01) |
| *G16H 40/63* | (2018.01) |

(52) U.S. Cl.
CPC ........... *G16H 20/13* (2018.01); *G06K 7/1417* (2013.01); *G06K 19/06037* (2013.01); *G06K 19/0723* (2013.01); *G06Q 50/01* (2013.01); *G16H 10/60* (2018.01); *G16H 40/63* (2018.01)

(58) Field of Classification Search
CPC ........ G16H 20/13; G16H 10/60; G16H 40/63; G06K 7/1417; G06K 19/06037; G06K 19/0723; G06Q 50/01

USPC ................................................... 340/539.12
See application file for complete search history.

(56) References Cited

U.S. PATENT DOCUMENTS

| | | | |
|---|---|---|---|
| 10,297,032 B2 | 5/2019 | Hanina et al. | |
| 10,552,575 B1* | 2/2020 | Mohebbi | G06F 18/22 |
| 11,664,103 B2 | 5/2023 | Low | |
| 2002/0194029 A1* | 12/2002 | Guan | G06Q 10/10 |
| | | | 705/3 |
| 2008/0311968 A1 | 12/2008 | Hunter | |
| 2013/0182295 A1 | 7/2013 | Naaman | |
| 2014/0180719 A1* | 6/2014 | Bell | G16H 10/60 |
| | | | 705/3 |
| 2016/0132660 A1* | 5/2016 | Barajas | G16H 30/40 |
| | | | 705/2 |
| 2017/0147784 A1 | 5/2017 | Lohman | |
| 2018/0052958 A1* | 2/2018 | Crawford | G16H 40/63 |
| 2018/0315498 A1* | 11/2018 | Starr | A61J 7/0418 |
| 2020/0265938 A1 | 8/2020 | Low | |

(Continued)

FOREIGN PATENT DOCUMENTS

WO    2012151402 A1    11/2012

*Primary Examiner* — Kerri L McNally
(74) *Attorney, Agent, or Firm* — David J. Connaughton, Jr.; Justin P. Tinger; Yafei Xue

(57) ABSTRACT

The present disclosure contemplates a system and a medical device such as a smartphone or tablet that can operate as a secure medical device for tracking consumption of medications dispensed to patients by gathering and creating medical quality data about consumed medications that are accurate, precise, legally binding, and reliable. This medical quality data can be securely stored in a patient's digital medication diary.

19 Claims, 20 Drawing Sheets

(56) References Cited

U.S. PATENT DOCUMENTS

2021/0343404 A1* 11/2021 Hunt .................. G16H 10/60
2022/0233140 A1    7/2022 Weng

* cited by examiner

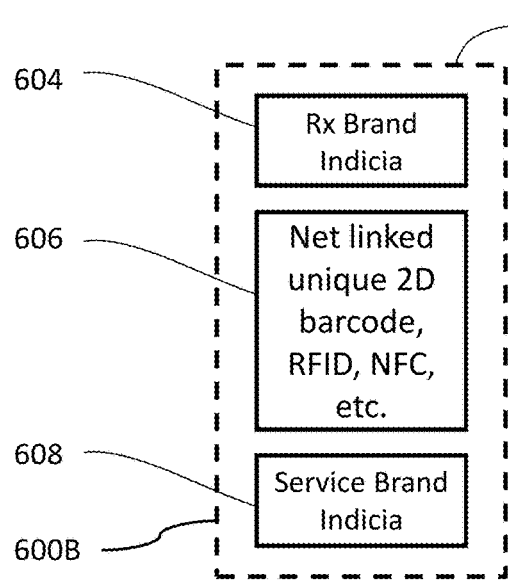
FIG. 6A.1
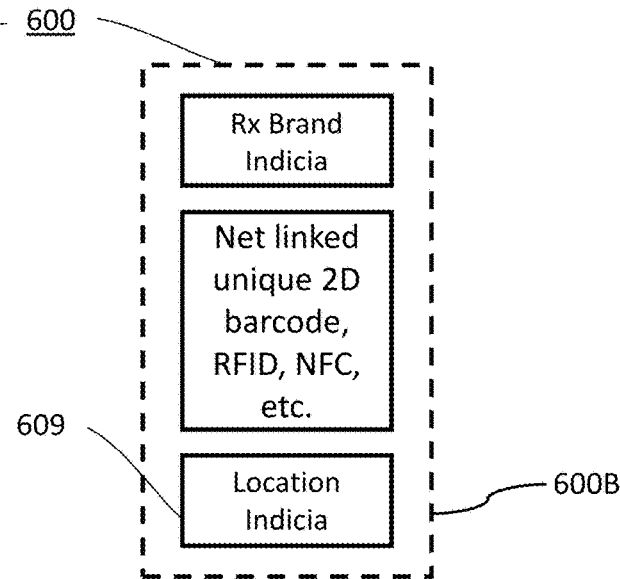
FIG. 6A.2
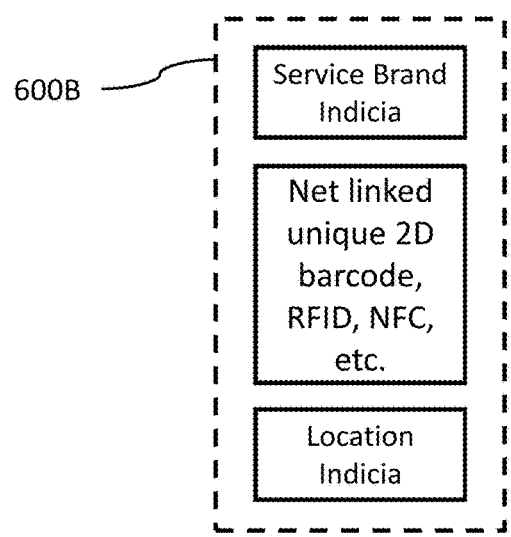
FIG. 6A.3
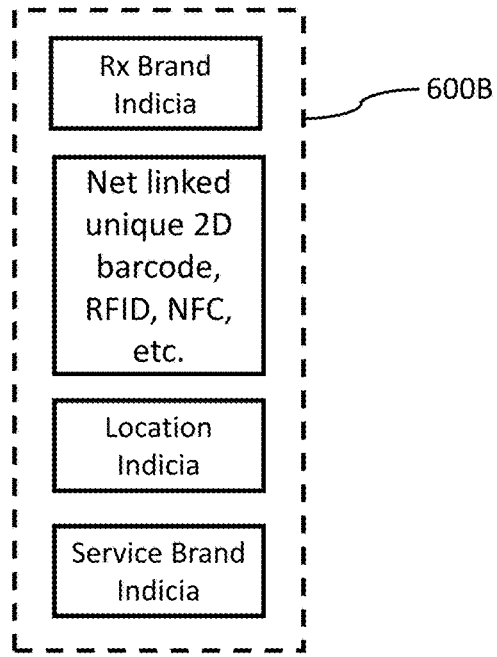
FIG. 6A.4

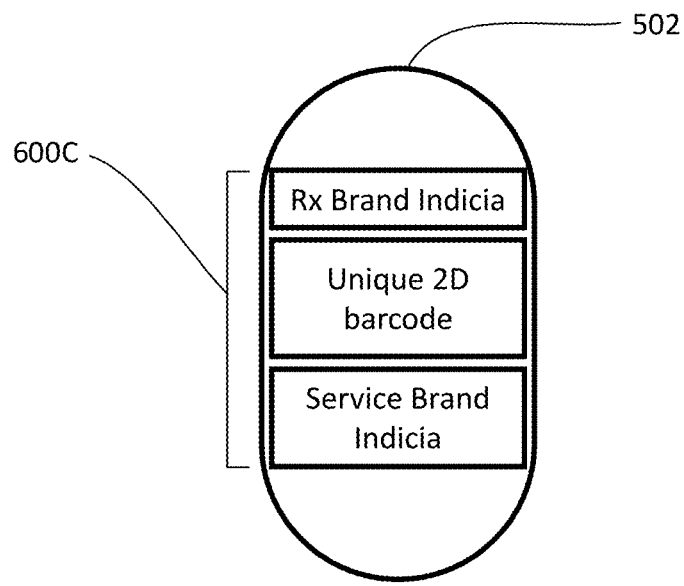
FIG. 6D.1
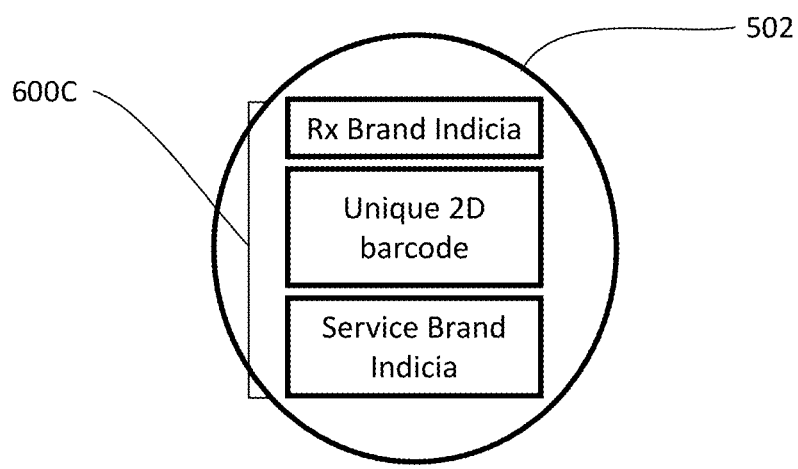
FIG. 6D2

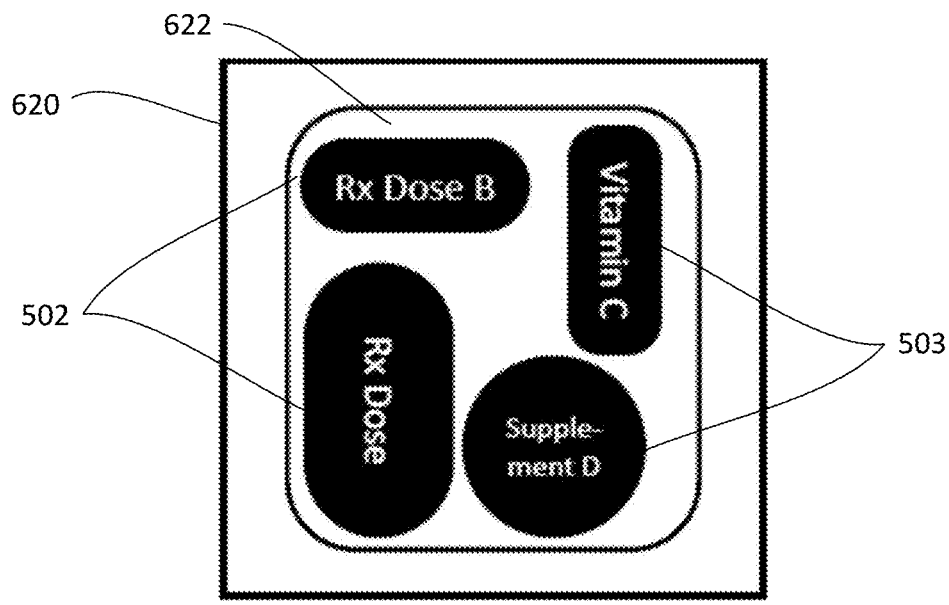
FIG. 6E.1
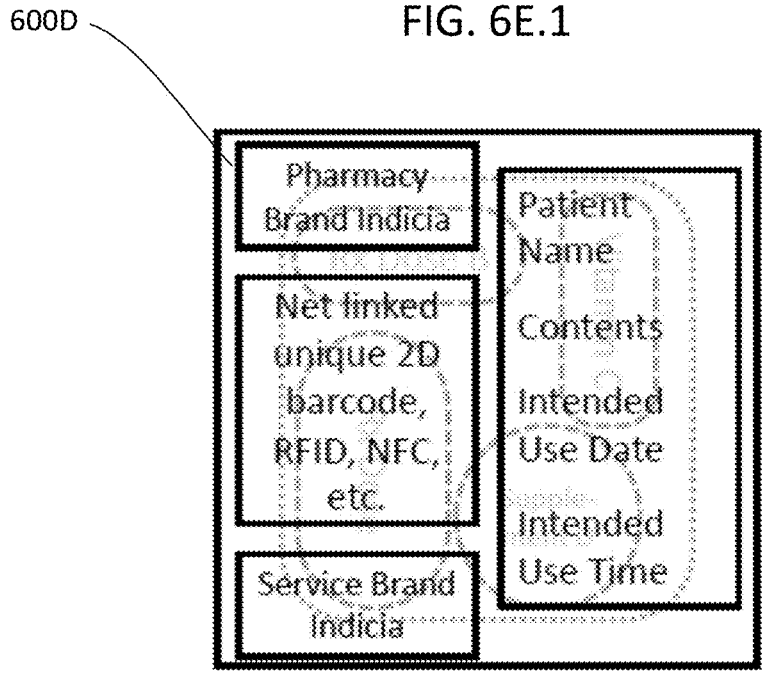
FIG. 6E.2

AUTHENTICATION METHODS AND SYSTEMS FOR DISPENSED PRESCRIPTIONS

CROSS-REFERENCE TO RELATED APPLICATIONS

This application claims the benefit of U.S. Provisional Patent Application No. 63/446,812 filed on Feb. 18, 2023; which is herein incorporated by reference in entirety.

FIELD OF INVENTION

The present invention relates to a computerized medical device, system, and method for helping patients to take their medications in the manner prescribed by their healthcare providers, to increase their persistence and adherence, and to a system and method to facilitate using smartphones and tablets to track actual dose consumption, and so forth.

BACKGROUND OF THE INVENTION

The current systems available for dispensing, tracking, and consumption of prescription drugs are limited in scope with regards to improving compliance of patients to use their prescription drugs when they should. Once a patient leaves the pharmacy with their dispensed prescription drugs, there are no controls and limited feedback and information about whether and when dispensed drugs are consumed. As a result, prescription drugs are often not taken as prescribed, with some studies showing that only about half of prescribed drugs are taken properly. Some patients do not take their drugs as long as prescribed (persistency), and some do not take the right dose at the right time (adherence). As a result, too many patients experience negative medical events, some severe, including death. The cost to the healthcare system and the economy of these unnecessary severe medical events are estimated to exceed $250 billion annually.

Current smartphones and tablets are powerful in their ability to help individuals and groups to manage a variety of complex and interrelated activities and processes, including in healthcare. However, their ability to help manage prescriptions dispensed to patients is limited because, while there is intense tracking of drug from manufacturing through to the dispensing pharmacists, there is little tracking beyond that point. Once dispensed there is limited ability to keep track of individual doses of medication. Absent this ability to monitor and track individual doses and their consumption, it is difficult to rely on other information and measures which only approximate consumption of medication.

The present application seeks to provide solutions to some of the above problems, by enabling smartphones and tablets to become medical devices which can enable increasing patient persistence and adherence for prescription drugs, which in turn can improve health care outcomes and reduce healthcare system costs.

SUMMARY OF THE INVENTION

The smartphone or tablet can become a secure medical device for medications dispensed to patients by gathering and creating medical quality data about consumed medications that are accurate, precise, legally binding, and reliable. This medical quality data can be securely stored in a patient's digital medication diary. This medical device for prescriptions dispensed to patients can use a patient's medication diary to help the patient to take the right drug at the right time through reminders and through the support of caregivers, family, friends, and medical providers. The medical device for prescriptions dispensed to patients can also provide personal or team games to encourage medication persistence and adherence. Financial incentives can also be initiated and tracked through the medical device for prescriptions dispensed to patients. The effect of patients' improved persistence (not stopping) and adherence (taking the right dose at the right time) can be improved medical outcomes for patients and lower healthcare system cost through fewer harmful and costly medical events. The medical device for prescriptions dispensed to patients can also be used for medical applications relative to the dispensed drug, including communicating with healthcare providers and prescription renewal. The medical device for prescriptions dispensed to patients can also enable positive collective activity including medication research, reduction of health care premiums, and social networking around common medications or conditions. The objective of this innovative method and device is to improve the health of patients and reduce overall healthcare costs.

DETAILED DESCRIPTION OF THE INVENTION

Figure 1A:
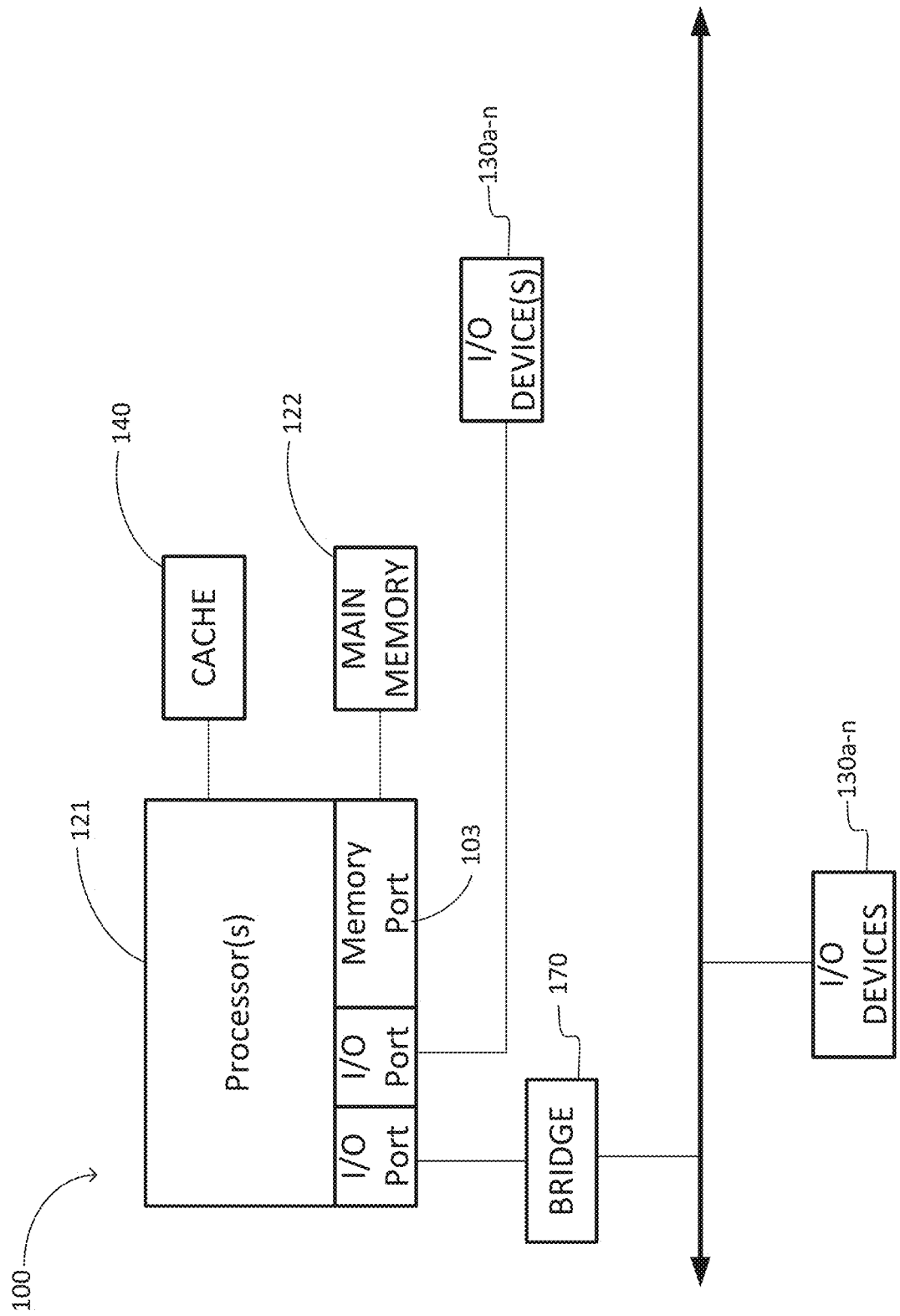
FIGS. 1A-1C are block diagrams depicting embodiments of computers, databases and networked systems useful in connection with the methods and systems described herein.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

One of the objectives of the present invention is to provide assistance to help patients take their medications as prescribed by tracking consumption of each dose. This is of particular importance for those who are reliant on their medications for ongoing health, including those with chronic conditions, the elderly, and those with mental health conditions. Another objective of the present invention is to establish a secure communication channel with patients that can further be utilized to communicate with medical providers and support persons.

What is needed is a system and method that can create accurate and reliable information about each individual medication dose as it is consumed. This accurate medical quality information can then be relied upon by the patient, caregivers, family, friends, healthcare providers, and third parties for medical and other legitimate purposes. It can also be incorporated into a secure application which enables the smartphone to become a computerized medical device which can advise patients and third parties.

This can all begin with the creation of a precise and reliable online medications diary. The precision and reliability of the medication diary can enable the medical device to initiate activities which can increase persistence and adherence for medications dispensed to patients, including for generic or branded drugs, including for the drugs and the indication(s) for which each drug is approved listed in the 44$^{th}$ edition (2024) of the FDA's Orange Book of *Approved Drugs with Therapeutic Equivalence Evaluations* which is incorporated herein in its entirety. A medications diary can be an accurate and authentic record of medications taken by a single patient, including a historical record of medications taken corresponding to the patient. The medications diary is stored on a memory accessible to the computerized medical device. Combining many medications diaries together can create a medications database. The medications diary and medications database can reside in the cloud, in a secure, HIPAA compliant database. It can only be accessed by the patient and those who have been given authorization by the patient.

The medications diary can include the data needed to track, measure, and manage dispensed medication use. It can include the patient's name and other identifying personal information, for example, date of birth, phone number, address, email, insurance information, and demographic information. It can include information about the patient's dispensed prescription, including prescriber identification, drug name, drug strength, dosage form, quantity prescribed, directions for use, date dispensed, quantity dispensed, dispensing pharmacy, dispensing pharmacy prescription number, and dispensing pharmacy phone number.

The medical device for prescriptions dispensed to patients can track that each dose of the dispensed medication was actually consumed at a specific date, time, and location. This can be done with a legally binding attestation by the patient. The legal attestation can be supported by evidence of the dose of medication and evidence of consumption.

As discussed further herein, there is a problem in the field of a lack of persistence and adherence to medicine dosing regimens. There is also a problem in the computerized field that it is easy to lie, manipulate, trick and otherwise fake or hack computerized systems due to a lack of verification and confirmation. This is a problem in all aspects of the computerized field as a computer system is only able to receive information and it is difficult to verify. The present invention solves this computerized problem in the medicine administration context by requiring evidence and/or attestation of taking the medicine, in addition to a simple confirmation which can be easily taken advantage of by a dishonest user.

The gathered evidence to confirm the dose of the medication may be done in any manner to confirm the taking of the medicine, a number of non-limiting examples follow. In one case, evidence of the dose of medication can be generated by using the medical device to take a picture of the medication consumed. Stronger evidence can be generated by having the patient enter into the device the pharmacy phone number and prescription number by scanning or manual input. For prescriptions which are dispensed in the manufacturer's packaging, even stronger evidence can be created by the patient using the camera of the medical device to scan the DSCSA GS1 datamatrix or manually the entering the dispensed package GTIN, serial number, expiration date, and lot number using the user input interface of the medical device. The strongest can be generated by a multi-factor dose authentication, where each dose is enclosed in an authenticable enclosure which requires an outside scan and possibly an inside scan. Multiple medications, vitamins and supplements can be sealed in the same enclosure, so long as they are to be consumed at the same time. The dose linkage to the legitimate prescription(s) for each patient can help confirm authenticity. Evidence of medication authenticity and dose consumption can be gathered through continuous video recording, which can start before outside authenticator scanning. In some embodiments, an artificial intelligence engine can review the recorded video to confirm that the medicine is taken. It can continue with breaking of the seal, removing the medication(s) from the enclosure, scanning the inside authenticator, and consuming of the medication(s). When multi-factor authentication is used with recording, attestation of the drug and consumption is also recorded at this point. The continuous recording can stop only after the patient shows that the medication(s) has been consumed. For example, with the continuous video of the smartphone medical device recording, the patient can swirl their tongue around their mouth and then open their mouth wide to show that the mouth is empty. Both front and back continuous video can be taken. If smartphone capability is limited, the two videos can be recorded interlaced at 15 fps each. The continuous video can include integrated audio using smartphone's microphone(s). In situations where there are questions about drug or consumption authenticity, all aspects of the recorded interaction can help to resolve uncertainties. Partial authentication of dose consumption can also be recorded well as non-consumption dose scans.

In a particular embodiment of creating a video record of medicine consumption, a user may use one or both of a front camera and a back camera of the computerized medical device, in this case a smartphone or tablet, using the camera(s) individually or simultaneously. The recording can start at the very beginning of the process, i.e. first taking the packaging of the medication, and record continuously through to a final attestation, and create a digital record of the evidence, the digital record being a data file saved on a memory accessible to the computerized medical device.

Inside and outside authenticators can provide evidence for two factor drug authentication. There can be a sealable enclosure for each dose or for multiple medications, vitamins, or supplements taken at the same time. Breaking of the seal can render a dose not authenticatable. Each authenticator can contain unique alpha-numeric characters. Authenticators can be scannable to internet addresses. Outside and inside authenticators can be linked to each other during packaging and recorded in the cloud or other accessible database.

Multi-factor authenticatable enclosures can be prepared by a pharmaceutical manufacturer. Authenticable doses can be linked to the sealed package DSCSA GS1 Data Matrix, which can typically be tracked through the supply chain through to the pharmacist. The pharmacist can link the DSCSA GS1 Data Matrix to the prescription number at time of dispensing, this linking can be recorded in the cloud or other accessible database.

Multi-factor authenticatable enclosures can also be prepared by the dispensing pharmacist. The pharmacist can place a single dose or multiple medications to be taken at the same time in an authenticatable enclosure which can have preprinted outside and inside authenticators. Outside and inside authenticators can be associated and recorded in a database when they were manufactured before they are supplied to the pharmacist. Outside authenticators can be linked to the dispensed prescription number by the pharmacist. Automation of the scanning and filling process can be used to improve efficiency.

The computerized medical device together with the digital medications diary created for patients and populations can improve our society by improving health care outcomes, improving economic results, and abating illegal drug trafficking activity. The medical device for prescriptions dispensed to patients can remind the patient when to take their medication. Specifically, the computerized medical device may be programmed to provide an output based on data in the medications diary of suggestions about taking medications, the suggestions based on prescription, medications history, and current date and time. Suggestions may include, but are not limited to audible reminders, reminders, suggestions, or tips presented on the display and/or as push notifications on the smartphone medical device, haptic reminders such as a vibration, automated messages to other devices such as a text message to a spouse, child, parent, caregiver, and the like, and information in these notifications to encourage habit forming behavior such as encouraging taking the medication along with a common event such as a meal, before bed, upon waking, after a shower, and so forth. These suggestions may be generated by a system server and sent via a network to the computerized medical device, or the medical device itself may be programmed to generate them based on the input information, and data gathered by one or more inputs received by the medical device. If patients are late in taking their medications, the medical device for prescriptions dispensed to patients can notify caregivers, family, or healthcare providers, who can contact the patient through the medical device to remind them to take the medication. Caregivers, family, or healthcare providers can also take other steps outside the medical device for prescriptions dispensed to patients to intervene as appropriate. When patients properly take their medications, caregivers, family, or healthcare providers can also provide positive reinforcement back to the patient through the medical device for prescriptions dispensed to patients. Through the medical device for prescriptions dispensed to patients, the patient can also be motivated through individual or team gamification. Gamification examples include, but are not limited to, individual or team games for patients to play on the computerized medical device which maintain or improve patience persistence and adherence. Through the medical device for prescriptions dispensed to patients, the patient can also receive rewards and/or financial incentives. In one embodiment, these incentives are presented to the patient via the user interface of the computerized medical device, and may be initiated via a prompt on a display of the computerized medical device and a receipt of an input to the user input interface, which can be relayed through third party networks by the computerized medical device. The result of these activities to increase persistency and adherence can provide patients with improved medical outcomes and lower overall medical costs. These reduced medical costs, typically for medical insurance companies, can in turn result in reduced premiums for individuals or group insurers, which are often employers.

The medical device for prescriptions dispensed to patients can enable remote monitoring and, where needed, control of patients taking medications. This can result in improved care given to those who are elderly or mentally compromised. It can also enable doctors to use automation to closely monitor the ongoing health of their patients on medications.

The medical device for prescriptions dispensed to patients can provide the most accurate medication consumption data to improve the quality of drug research. Researchers can know the exact drug, dose, date, and time of consumption by accessing the recorded data by the system. They can verify the authenticity of the drug and consumption of the medication from watching the multi-factor authentication process video which is recorded and saved as part of the patient record. The medical device for prescriptions dispensed to patients can enable a direct and immediate 2-way feedback channel between the patient and researchers. As such, the system is able use the gathered data, as well as inputs into the computerized medical device to enable a patient or population of patients the option to participate in medical research for conditions treated with prescription drugs.

The medical device for prescriptions dispensed to patients can enable the safer dispensing of controlled substances, like opioids. This can reduce the likelihood of addiction and provide a method of controlling the proper return or destruction of medications when the patient is finished their treatment. This can result in improved medical outcomes and a direct link to healthcare practitioners if issues arise. The medical device for prescriptions dispensed to patients can help those recovering from addiction to drugs, including opioids, to track their progress and communication directly with caregivers, family, friends, and healthcare providers.

The medical device for prescriptions dispensed to patients can abate controlled medications trafficking, especially opioids by tracking scans of all doses. It can also abate counterfeit medication production and distribution.

The medical device for prescriptions dispensed to patients can foster common medication and disease communities enabling patients and family to connect, share, and improve their experience with specific medications and disease conditions.

The data in each digital medication diary is owned by the patient. The patient may authorize others to have access to all or part of the data in their medication diary. The patient may revoke their authorization(s). Examples of authorizations to give access to others include caregivers, family, friends, healthcare providers, medical researchers or healthcare insurers.

Other objectives will also be noted to those of ordinary skill in the art as the various embodiments of systems and methods are described below. In some embodiments, the methods and systems described herein relate to dispensed medication tracking, increasing persistency, increasing adherence, and improving healthcare outcomes, and reducing healthcare costs. Before describing such methods and systems in detail, however, a description is provided of a computer and a network in which such methods and systems may be implemented.

Figure 1B:
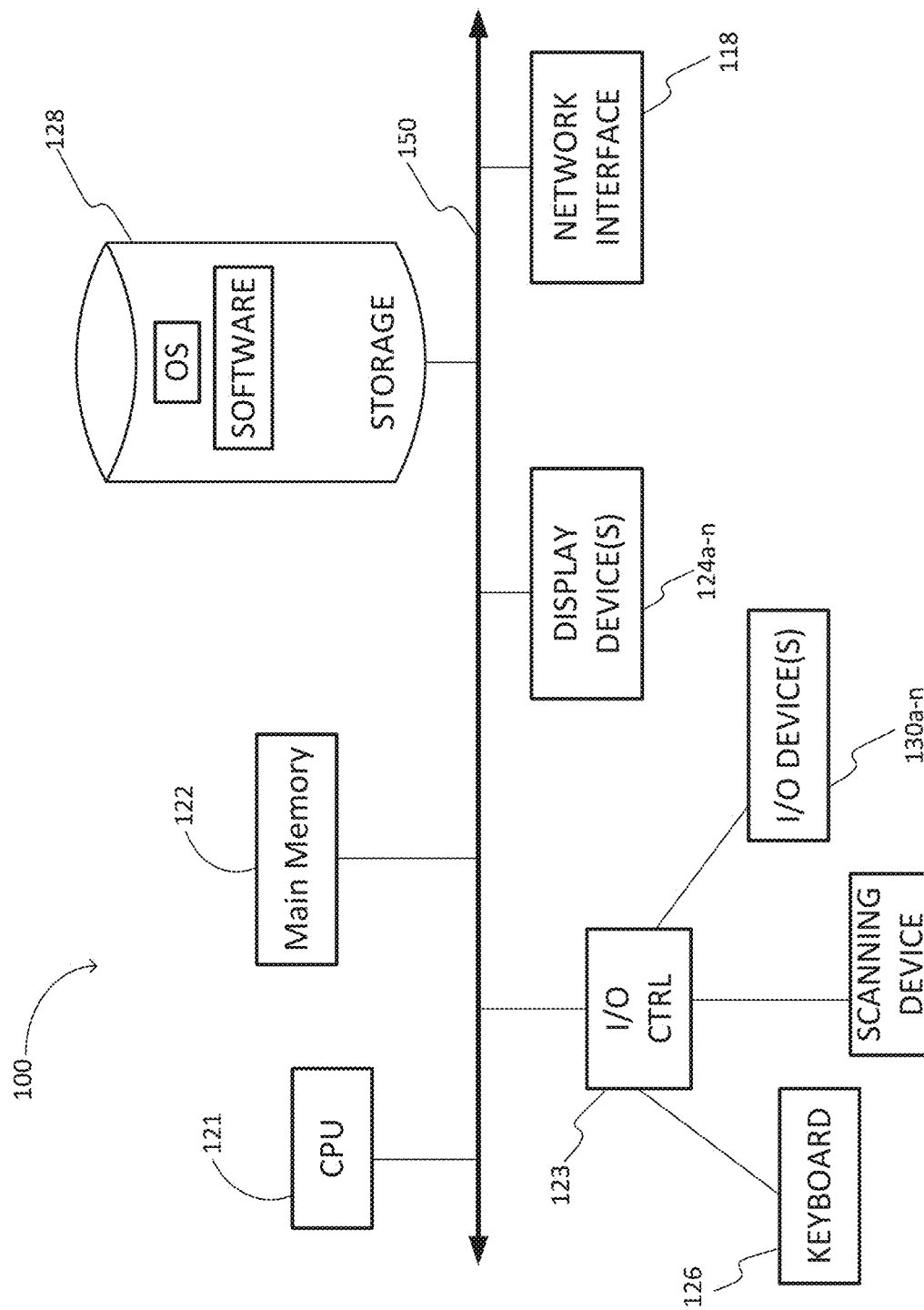

Referring to FIGS. 1A and 1B depict block diagrams of components of the computerized medical device, or smartphone/tablet configured as a computerized medical device contemplated in this disclosure and discussed throughout this disclosure. A computing device 100 used herein as the computerized medical device may utilize the user interface 102a-c and/or a computing device 106a-c, shown in FIG. 1C. As shown in FIGS. 1A and 1B, each computing device 100 includes a central processing unit 121, and a main memory unit 122. As shown in FIG. 1B, a computing device 100 may also include a storage device 128, a network interface 118, an I/O controller 123, display devices 124a-n, a keyboard 126 which may be in the form of a digital keyboard presented on a touch screen display, a scanning device 127, such as a camera(s) or 2D barcode scanner, and one or more other I/O devices 130a-n such as a mouse, trackpad, pen, RFID reader/writer and so forth. The storage device 128 may include, without limitation, an operating system and software. As shown in FIG. 1A, each computing device 100 may also include additional optional elements, such as a memory port 103, a bridge 170, one or more input/output devices 130a-n (generally referred to using reference numeral 130), and a cache memory 140 in communication with the central processing unit 121. These components communicate with the central processing unit 121 which comprises programming operable to control these components, and, when appropriate, save data to the memory unit 122 and/or send data through the network interface 118, and the like.

The central processing unit 121 is any logic circuitry that responds to and processes instructions fetched from the main memory unit 122. In many embodiments, the central processing unit 121 is provided with one or more microprocessor units such as: those manufactured by Intel® Corporation, Motorola® Corporation, International Business Machines®, Advanced Micro Devices®, Qualcomm®. The computing device 100 may be based on any of these processors, or any other processor capable of operating as described herein.

Main memory unit 122 may be one or more memory chips capable of storing data and allowing any storage location to be directly accessed by the microprocessor 121. The main memory 122 may be based on any available memory chips capable of operating as described herein. In the embodiment shown in FIG. 1B, the processor 121 communicates with main memory 122 via a system bus 150. FIG. 1A depicts an embodiment of a computing device 100 in which the processor communicates directly with main memory 122 via a memory port 103. FIG. 1A also depicts an embodiment in which the main processor 121 communicates directly with cache memory 140 via a secondary bus, sometimes referred to as a backside bus. In other embodiments, the main processor 121 communicates with cache memory 140 using the system bus 150.

In the embodiment shown in FIG. 1B, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1A depicts an embodiment of a computer 100 in which the main processor 121 also communicates directly with an I/O device 130b via, for example, HYPERTRANSPORT, RAPIDIO, or INFINIBAND communications technology.

The computerized medical device, i.e. computing device 100 may comprise or be connected to one or more of a wide variety of I/O devices 130a-n, each of which may be of the same or different type and/or form. Input devices include touch screens, keyboards, mice, trackpads, trackballs, microphones, scanners, cameras, RFID readers/writers and drawing tablets. Output devices include video displays including touch screens, speakers, inkjet printers, laser printers, and dye-sublimation printers. The I/O devices may be controlled by an I/O controller 123 as shown in FIG. 1B. Furthermore, an I/O device may also provide storage and/or an installation medium for the computing device 100. In some embodiments, for example, the computing device 100 may provide USB connections (not shown) to receive handheld USB storage devices.

Referring still to FIG. 1B, the computing device 100 may support any suitable installation device (Not Shown), such as a floppy disk drive for receiving floppy disks such as 3.5-inch disks, 5.25-inch disks or ZIP disks, a CD-ROM drive, a CD-R/RW drive, a DVD-ROM drive, tape drives of various formats, USB device, hard-drive or any other device suitable for installing software and programs. The computing device 100 may further comprise a storage device, such as one or more hard disk drives or redundant arrays of independent disks, for storing an operating system and other software.

Figure 1C:
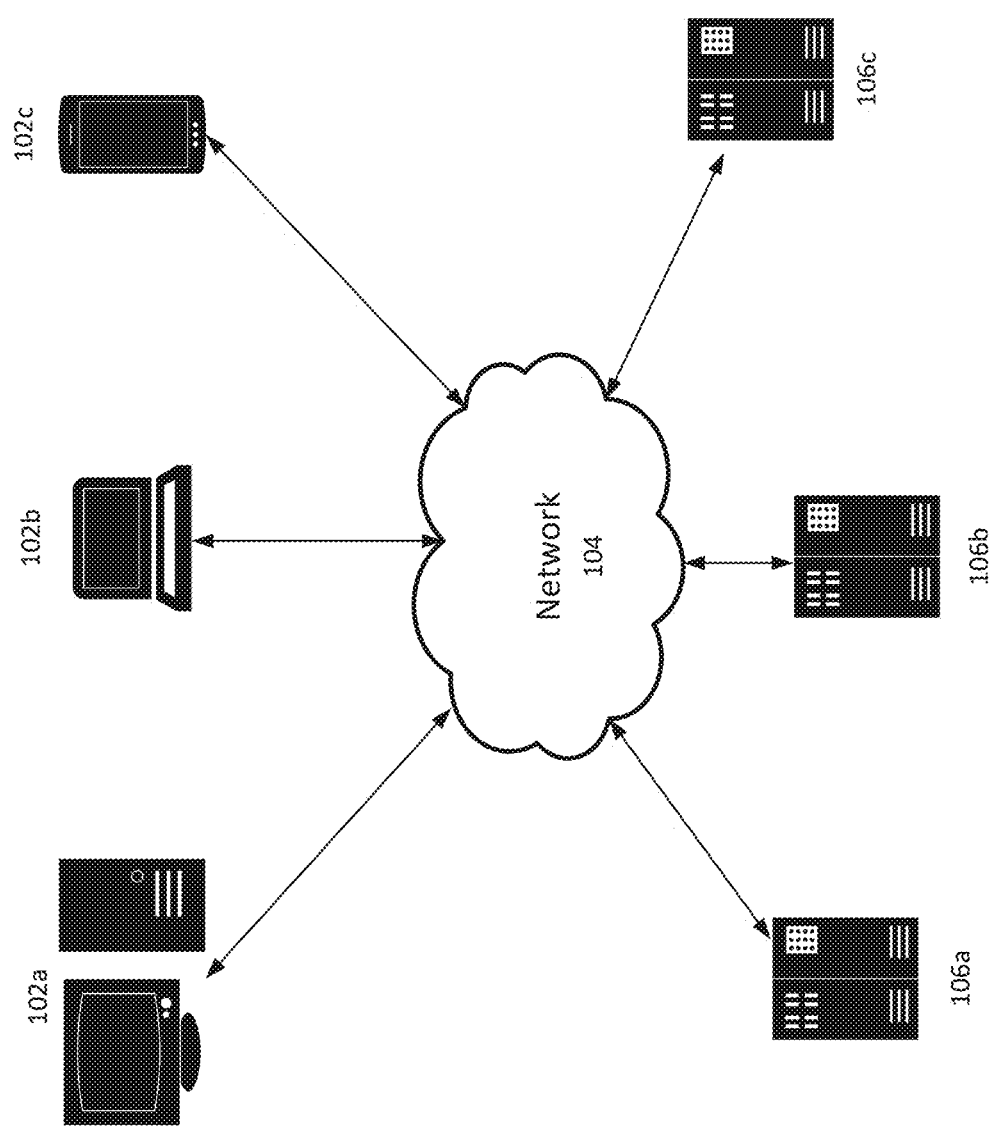

Furthermore, the computing device 100 may include a network interface 118 to interface to the network 104 shown on FIG. 1C through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, EEE 802.11, IEEE 802.11a, IEEE 802.11b, IEEE 802.11g, IEEE 802. Ln. CDMA, GSM, WiMax, and direct asynchronous connections). In one embodiment, the computing device 100 communicates with other computing devices 100' via any type and/or form of gateway or tunneling protocol such as Secure Socket Layer (SSL) or Transport Layer Security (TLS). The network interface 118 may comprise a built-in network adapter, network interface card, PCMCIA network card, card bus network adapter, wireless network adapter, USB network adapter, modem, or any other device suitable for interfacing the computing device 100 to any type of network capable of communication and performing the operations described herein.

In further embodiments, an I/O device 130 may be a bridge between the system bus 150 and an external communication bus, such as a USB bus, a FireWire bus, an Ethernet bus, a Gigabit Ethernet bus, a HIPPI bus, a Super HIPPI bus, a SerialPlus bus, a SCI/LAMP bus, a FibreChannel bus, or a Serial Attached small computer system interface bus, or any other type of bus currently available or to be created using the same architecture.

A computing device 100 of the kind depicted in FIGS. 1A and 1B typically operates under the control of operating systems, which control scheduling of tasks and access to system resources. The computing device 100 can be running any operating system such as any of the versions of the MICROSOFT WINDOWS operating systems, UNIX and LINUX operating systems, any version of the MAC OS, ANDROID operating system, IOS operating system, any real-time operating system, any open source operating system, any proprietary operating system, any operating systems for mobile computing devices, or any other operating system capable of running on the computing device and performing the operations described herein.

FIG. 1C illustrates an embodiment of a network environment. The network environment comprises one or more clients 102a-102c (also generally referred to as local machine(s) 102, client(s) 102, client node(s) 102, client machine(s) 102, client computer(s) 102, client device(s) 102, computing device(s) 102, endpoint(s) 102, or endpoint node(s) 102) in communication with one or more computing devices 106a-106c (also generally referred to as server(s) 106 or computing device(s) 106) via one or more networks 104.

The network 104 (also generally referred to as network(s) 104) can be a local-area network (LAN), such as a company Intranet, a metropolitan area network (MAN), or a wide area network (WAN), such as the Internet or the World Wide Web. In some embodiments, there are multiple networks 104 between the client 102 and the computing devices 106. In one of these embodiments, a network 104 may be a private network or a public network. As shown in FIG. 1C, a client 102a device on a network 104 may connect to other client devices 102b-c or to other computing devices 106a-c via one or more networks 104.

The network 104 may be any type and/or form of network and may include any of the following: a point-to-point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. The network may comprise mobile telephone networks utilizing any protocol or protocols used to communicate among mobile devices, including AMPS, TDMA, CDMA, GSM, GPRS, or UMIS. In some embodiments, different types of data may be transmitted via different protocols. In other embodiments, the same types of data may be transmitted via different protocols.

A client 102 and a computing device 106 (referred to generally as computing devices 100) can be any workstation, desktop computer, laptop or notebook computer, server (including file servers, application servers, and media servers), portable computer, mobile telephone or other portable telecommunication device, media playing device, a gaming system, mobile computing device, smartphone, tablet computer, or any other type and/or form of computing, telecommunications or media device that is capable of communicating on any type and form of network and that has sufficient processor power and memory capacity to perform the operations described herein. In some embodiments, the computing device 100 may have different processors, operating systems, and input devices consistent with the device. Typical embodiments of the present invention, however, are carried out on smartphones or tablet computer devices configured and programmed to operate as the computerized medical device disclosed herein.

A client 102 i.e. a user may execute, operate or otherwise provide an application, which can be any type and/or form of software, program, or executable instructions, including, without limitation, any type and/or form of web browser, web-based client, client-server application, HTML, an ActiveX control, or a JAVA applet, PHP, and Javascript, or any other type and/or form of executable instructions capable of executing on client 102. Examples of browsers include INTERNET EXPLORER®, EDGE®, CHROME®, FIREFOX®, SAFARI® and other browsers known.

A computing device 106 may utilize a file server, application server, web server, proxy server, appliance, network appliance, gateway, application gateway, gateway server, virtualization server, deployment server, SSL VPN server, or firewall. In other embodiments, a computing device 106 is a blade server. In further embodiments, the computing device may be a virtualized server operating one processor of a multi-processor system. In some embodiments, the functionality described herein is provided as a virtual application using a virtualized processor.

In one embodiment, a computing device 106 provides functionality of a web server. In some embodiments, a web server 106 comprises an open-source web server.

As will be described below various tasks and steps can be processed on one or more computing devices 106, as well as clients 102. The processes and steps can be bifurcated across each, for example, retrieval of information from the medications diary can performed on 106, where request or query information can be received and analyzed by 106c. In some instances, clients 102a, b or c could also be assisting in real-time processing in the various steps or simply be the triggering device or interface to retrieve and/or initiate the processing of various steps as will be described below.

It should also be clear that the present embodiments can be based and operated in the cloud or cloud-based systems, of which several known cloud computing platforms that exist include Amazon Web Services® (AWS), Microsoft's Azure®, and IBM's Cloud®.

Figure 2:
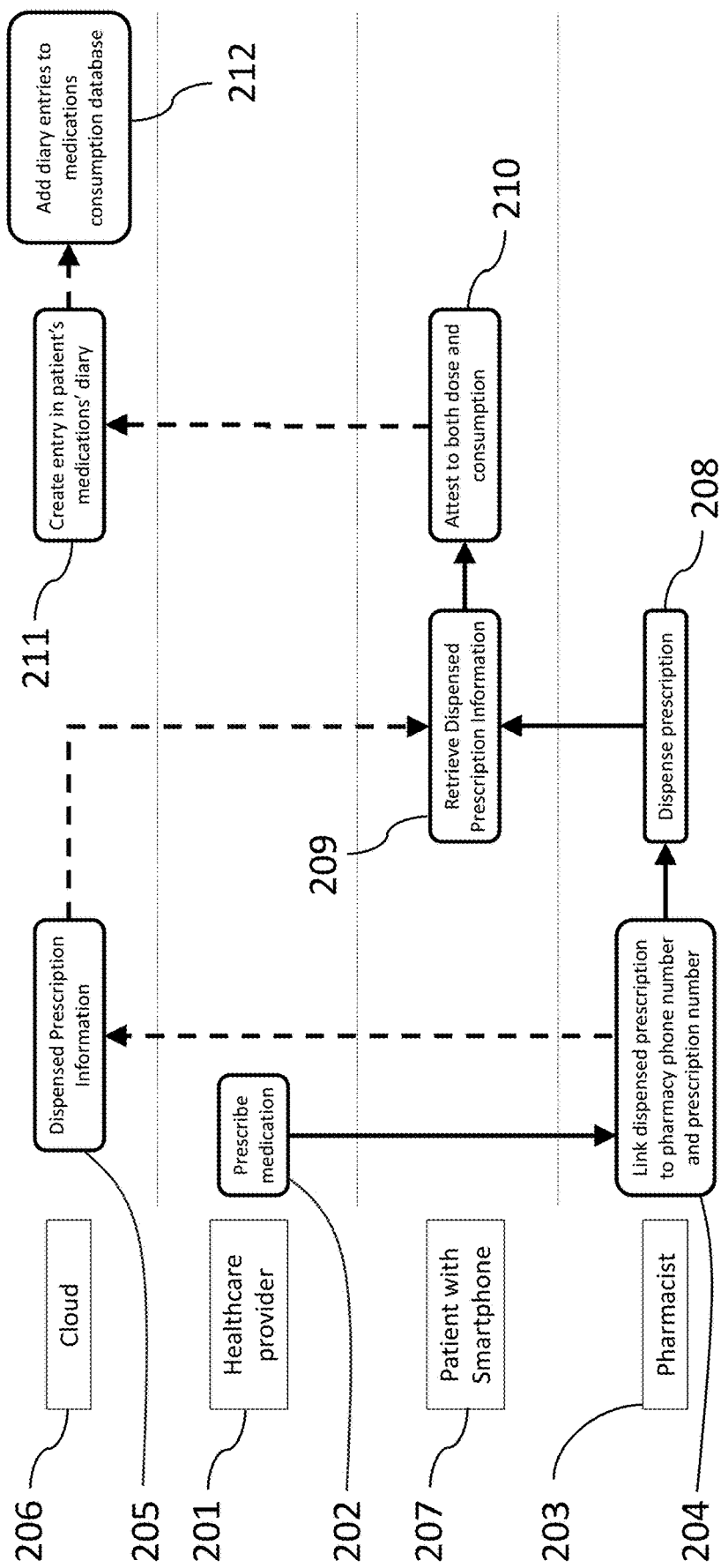
FIG. 2 illustrates a flowchart of a method of using the medical device for prescriptions dispensed to patients.

Referring to FIG. 2, the healthcare provider 201 can prescribe medication 202 for the patient. During the dispensing process by the pharmacist 203, the pharmacy phone number and the specific prescription number can be linked 204 to the dispensed prescription information and stored 205 in the cloud 206. After the patient 207 receives the dispensed medication 208, the patient 207 can use the computing device, in this embodiment, a smart phone, to retrieve the dispensed prescription information 209 by entering or scanning the pharmacy phone number and the unique prescription number. When the patient 207 takes their prescribed medication, the patient 207 can use their smartphone to attest 210 that this was the drug dispensed and that they are taking the drug at this date and time. An entry can be created 211 in the patient's medications diary, which can become part of the medications consumption database 212.

Figure 3:
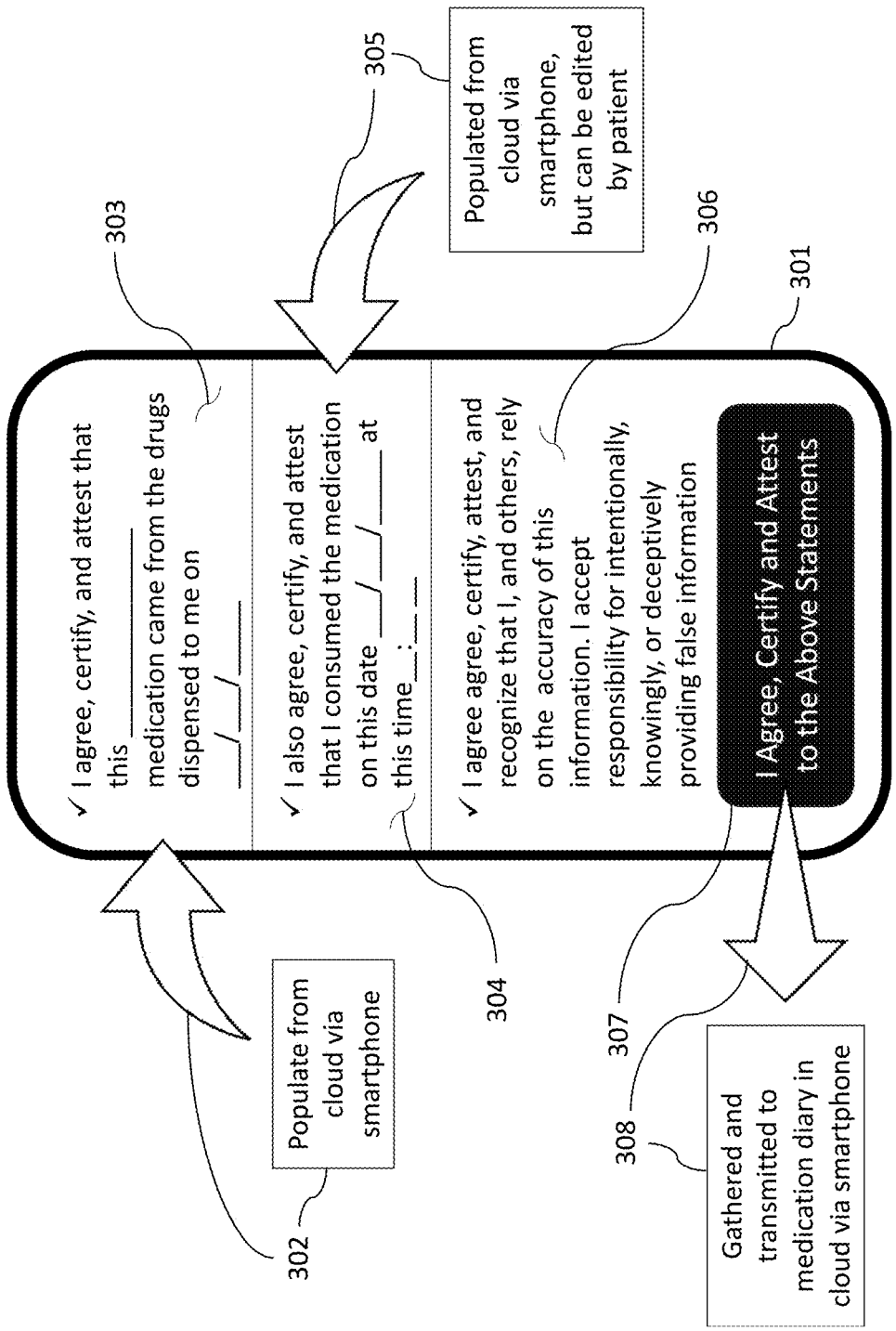
FIG. 3 illustrates a screenshot of various patient attest statements.

Referring to FIG. 3, the patient can use their smartphone 301 to retrieve prescription information and populate 302 an attestation statement 303 that the dispensed drug is consumed. Similarly, an attest statement 304 of date and time of consumption can be populated 305 from the smartphone operating system and edited, and edits can be noted in the record. The patient can also attest 306 to the integrity of the information provided. The patient can press the statement 307 to certify all onscreen attestations which also transmits 308 the information to the patient's medication diary in the cloud. In operation, the attestation is automatically generated by the programmed computerized medical device, which is operable to generate and display the attestation document and a prompt to provide a confirming input into the user interface to attest to the consumption of the medication. The prompt may, in either a single or multi-prompt process, provide a prompt to confirm the date and time that the patient consumed the medication. The attestation document may be saved to the patient's medication diary, which includes a digital record of medical prescription information and patient attestations of which medications are taken and when the medications are taken, the digital record being a data file saved on a memory accessible to the computerized medical device.

In a preferred embodiment, the attestation document is automatically generated in the system by the user interface and is signable and recordable all within the user interface of the system. This prevents a user from having to navigate away into, e.g. a browser signature program, third party system, or the like. This solves the problem in the computer arts of having to navigate away from a browser/user interface, which often leads to failure of the user to return to the user interface, which could lead a problem of reduced persistence and adherence to the medication administration regimen.

In some embodiments, the computerized medical device is operable to receive and record evidence that the patient has dispensed and taken the medication. The device may then append this gathered evidence data to the attestation, linking the two and saving this data to the patient's medications diary. In one embodiment, evidence of the patient's attestation that medication was dispensed to the patient can be received from the patient by the computerized medical device by operating the computerized medical device to take a photo of the drug or bottle using the camera; scanning, using the camera of the computerized medical device or entering, using the user input interface of the computerized medical device, one or more of: the pharmacy phone number and prescription number; the dispensed package DSCSA GS1 datamatrix, the dispensed package GTIN, serial number, expiration date, and lot number, a dose to confirm single factor authentication of the medication; and/or a dose to confirm multi-factor authentication of the medication.

Figure 4A:
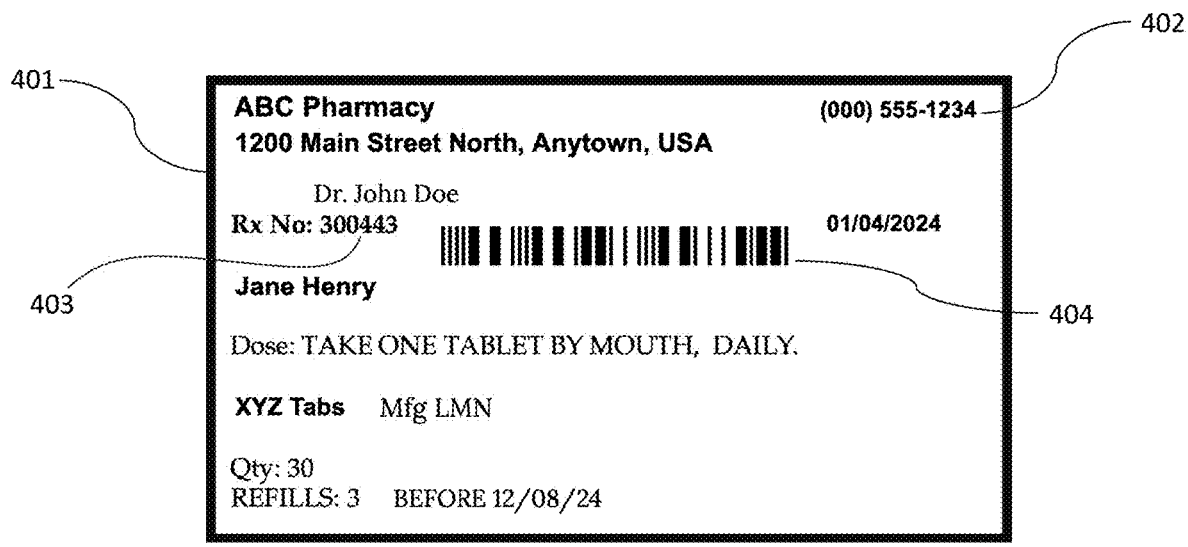
FIGS. 4A-4B illustrate dispensed prescription labels.

Referring to FIG. 4A, is a sample prescription label 401 which is typically attached to the dispensed medication package, bottle, or container. The patient can link to their prescription using their smartphone as the computerized medical device to enter the pharmacy phone number 402 and the prescription number 403. Alternatively, the patient can link to their prescription using their smartphone to enter the pharmacy phone number 402 and to scan, using a camera, the prescription number barcode 404. Often the barcodes 404 are part of internal pharmacy numbering and database system. The pharmacy phone number can be used to identify the type of pharmacy such as CVS®, RITEAID® and other sources to understand the type of pharmacy numbering system utilized for interpreting the barcode, so as to appropriately translate those numbers or to retrieve the specific prescription associated with that number.

Figure 4B:
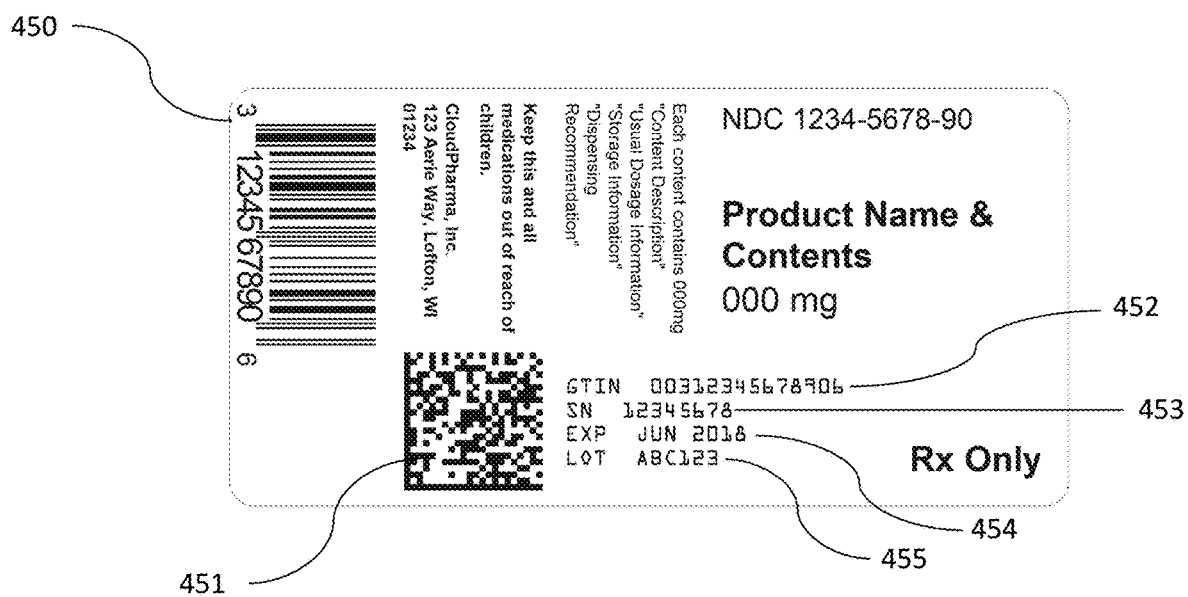

Referring to FIG. 4B, the medication can be dispensed in the package that was sold to the pharmacy, in which case it can contain required DSCSA information 450. In this situation, the patient can link to their prescription using their smartphone to scan, using a camera, the unique GS1 DataMatrix 451. Alternatively, patient can link to their prescription using their smartphone to enter the GTIN number 452, the serial number 453, the expiration date 454, and the lot number 455. As discussed throughout, the input data into the computerized medical device may be stored in a memory and/or database, whether on the device or through a networked connection.

Figure 5A:
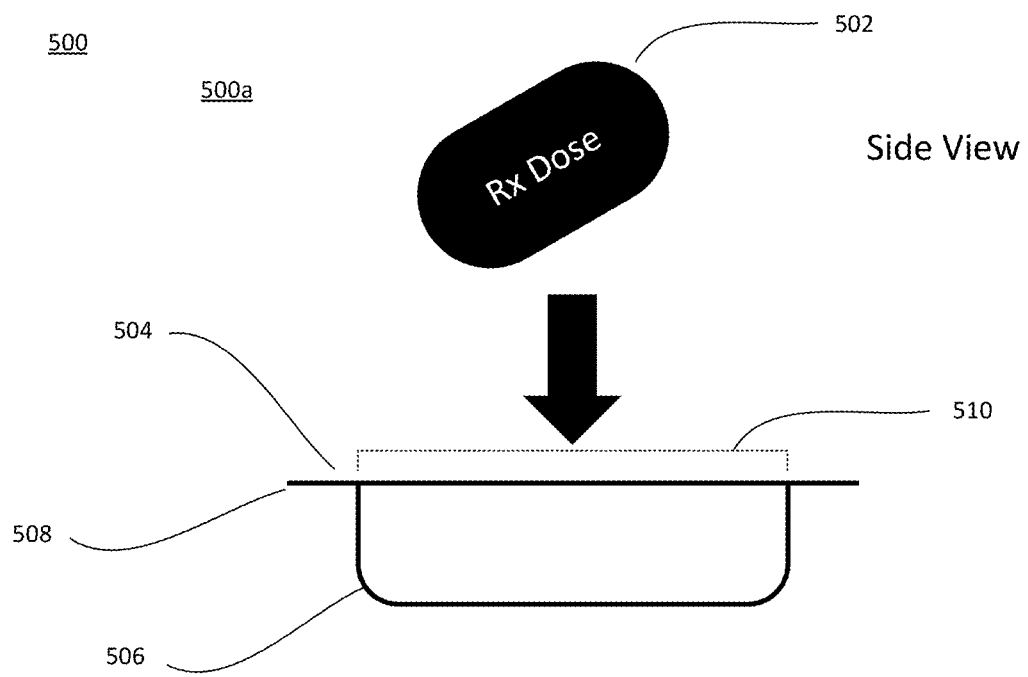
FIGS. 5A-C illustrate various views of dose containers used to store and then later dispense medications.
Figure 5B:
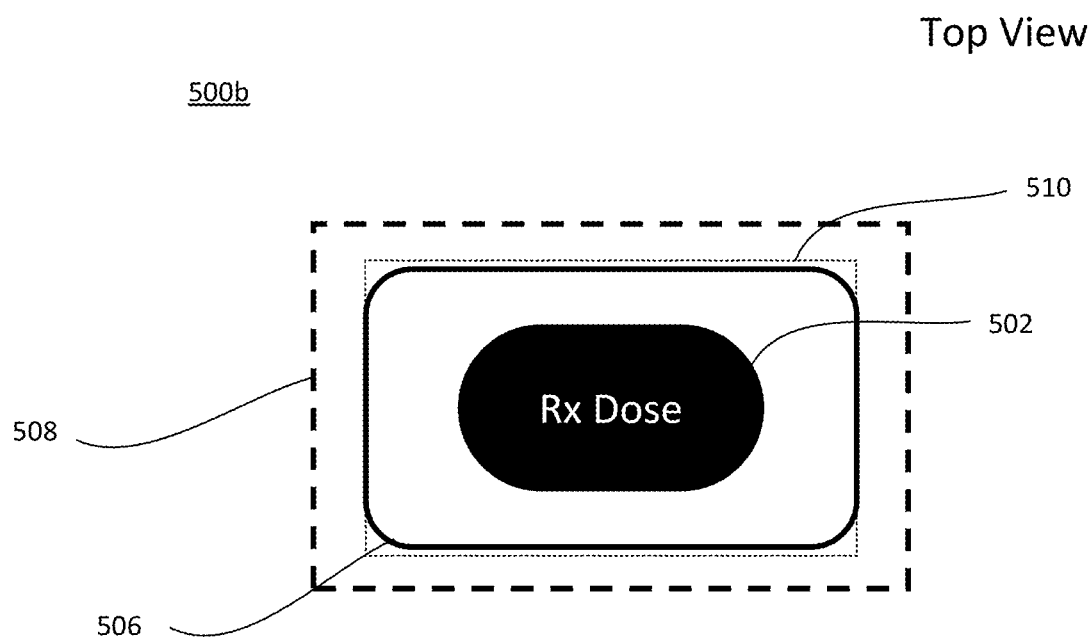

FIGS. 5A-B Illustrate various views of an authenticatable dose container 500 used to store and then later dispense medication. A top view of dose container in configuration 500a is shown where a dose of medication 502 can be placed therein. FIG. 5B illustrates a configuration 500b with the dose of medication 502 disposed inside a cavity portion 506 that is connected to support layer 508. A sealing layer 504, which may be comprised of multiple layers of material, can be disposed over the support layer 508. An observable surface can be formed in part by sealing layer 504 that is provided over the cavity 506, wherein the dose of medication 502 is to be stored for shipping and later dispensing.

Some common dose containers include blister packs, which can provide one or more cavity portions aligned in a matrix having X number of rows and Y number of columns. Some blister packs have different configurations such as circular shapes and so forth that are formed of the plurality of cavities or blisters. Other dose containers that are known to the those skilled in the art include rolls, jars, bottles, vials, droppers, cartridges, syringes, and packets. The computerized medical device, in this and other embodiments discussed, is programmed to read and identify data on the authenticatable dose container 500 by, for example, image analysis as recorded by a camera photo or video, or other wireless communication such as RFID detection, and the like.

Figure 5C:
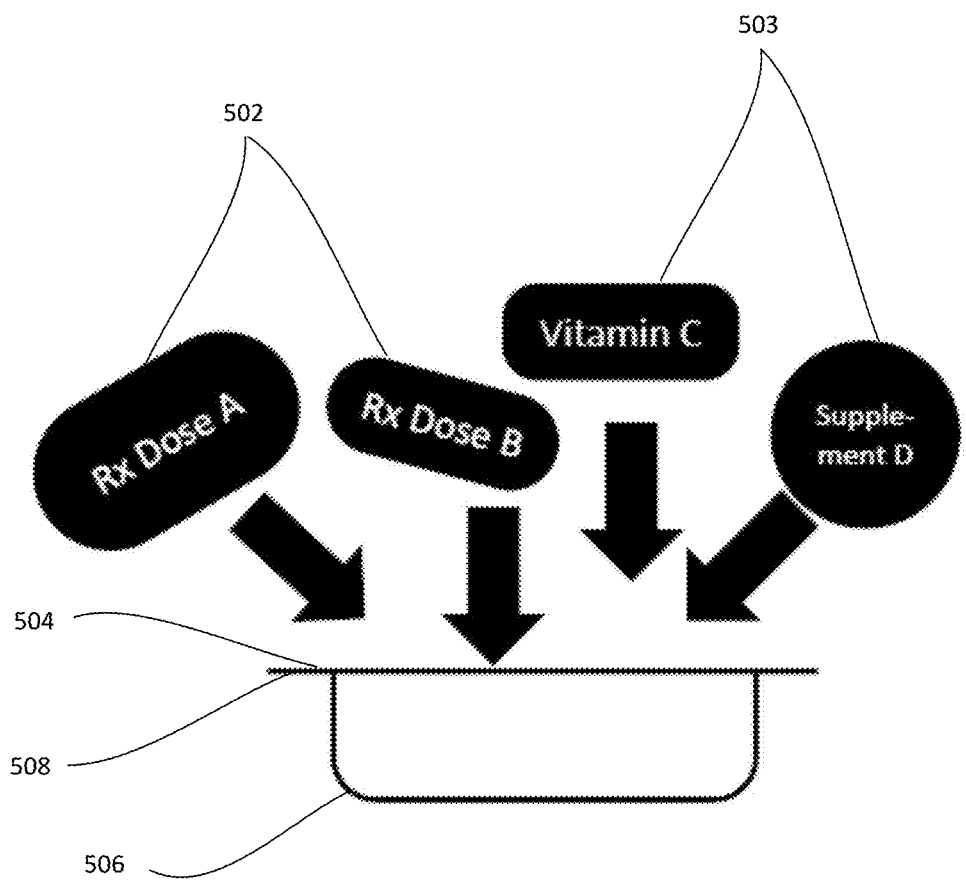

FIG. 5C illustrates another dose container like those of FIGS. 5A-C but configured to store doses of multiple medications 502 and doses of multiple vitamins or supplements 503 in the same cavity 506. It is common for patients to take a prescribed cocktail of medications, vitamins, and supplements as part of their health regiment. Increasingly there are dose containers that combine, where possible, multiple types of medications, vitamins, and supplements for convenience and to assist with adherence.

An authenticator indicia, such as the example shown in FIG. 6A.1 can be disposed on or within the dose container packaging to be used as part of the systems and methods herein for authenticating doses of medication and tracking doses of medication. The authenticator indicia 600 can be comprised of one or more sections, such as section 604 that is a brand indicia, which is indicative of the manufacturer of the dose of medication, section 606 as shown can be contain a unique identification number, linked to a website, that can be encoded into a 2D barcode or matrix, a 1-D barcode, electronically as an RFID tag, or other NFC, active or passive radio frequency tag, or electromagnetic spectrum emitting or responsive tag that is readable and recordable by the smartphone computerized medical device. Section 608 can comprise indicia associated with the brand of the service company providing the authentication systems or methods. Alternatively, a fourth indicia can be disposed thereon, such as a regional or location indicia 609. The regional indicia 609 can be indicative of an authorized distribution region, consumption region, or manufacturing region where the dose of medication is allowed to be distributed to, consumed in, or manufactured in. For example, the regional indicia can include a country name or a state name, that indicates the authorized distribution of that particular dose of medication in that country or state. Thus, if a user were to see the country Japan on the authenticator indicia on a dose container and they were in the United States, it might give them pause with regards to the ability to have, distribute or consume that particular dose of medication. It might also be indicative of the governing laws or standards by which that particular dose of medication was approved or authorized.

FIGS. 6A.2-6A.4 illustrate other variations and combinations for exemplary purposes, but are not intended to be limiting in scope, as additional variations can be contemplated to those skilled in the art upon presenting these examples.

In a particular embodiment, the outside authenticator on a blister pack or sealed enclosure containing at least one dose of medication can be used for authentication that the medicine was taken. For example, the computerized medical device may be operable to associate the outside authenticator of each blister pack or sealed enclosure with each dose of medication in a database. Then, the device may associate, in a database, each outside authenticator with other outside authenticators within the same unit of sale, at manufacture, wholesale, or retail. The medical device may scan the outside authenticator, using the camera and then provide an authenticating communication system configured to receive scanned information from the outside authenticator. The medical device may be further programmed to determine whether the dose of medication is authentic based on available data, and to display medication authentication confirmation on the display of the computerized medical device.

Figure 6B:
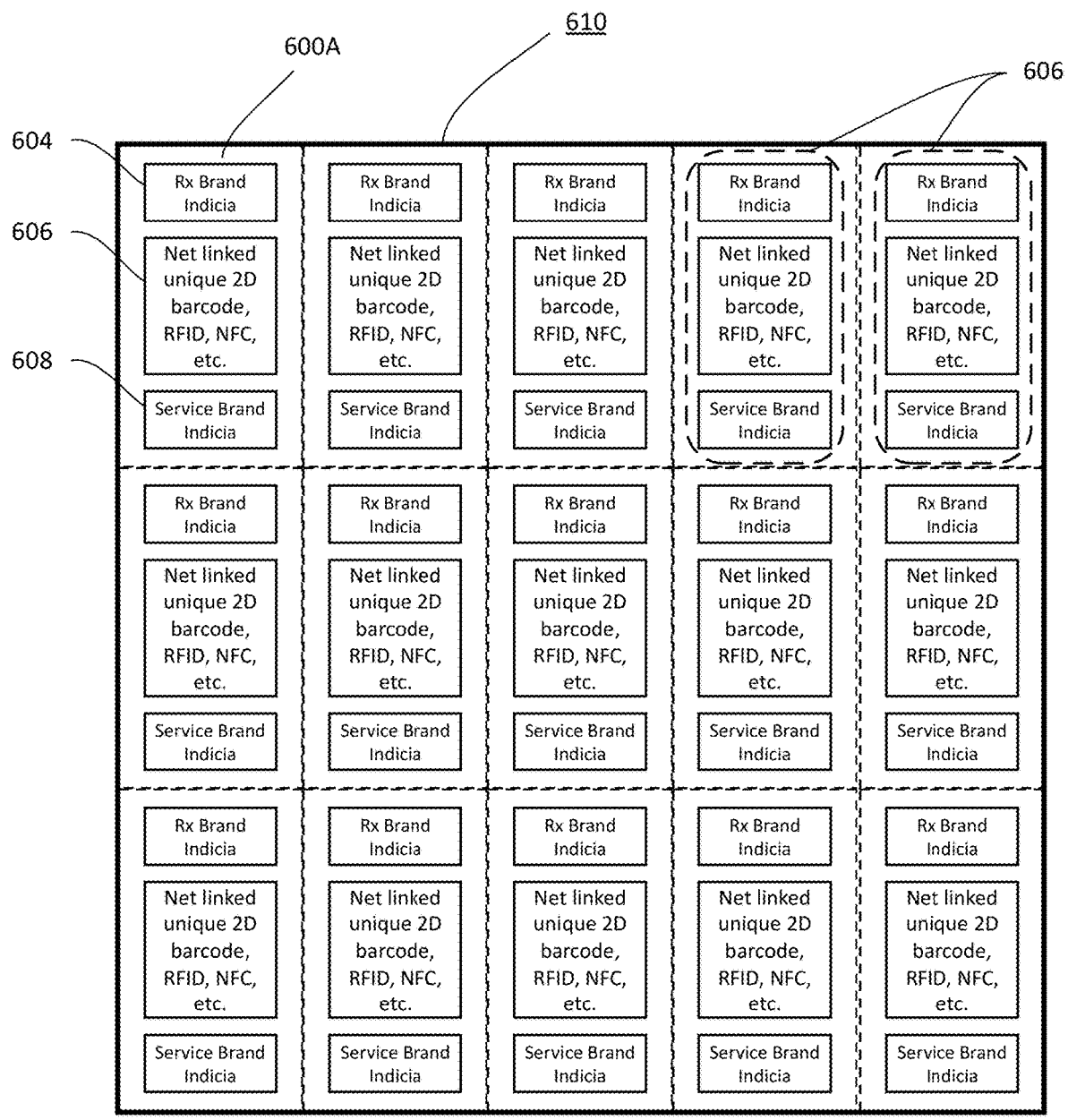
FIGS. 6A.1-6C illustrate examples of authenticator indicia and positions where the authenticator indicia may be placed on a dose container.
FIGS. 6D.1-6D.2 illustrate yet another example of an authenticator indicia being placed on to the dose of medication itself.
FIGS. 6E.1-6E.2 illustrate yet another example of an authenticator indicia being placed on a multi-dose/vitamin/supplement dose container.

In FIG. 6B a sheet 610 of authenticator indicia 600A can be disposed over a dose container, such as a blister pack, having a plurality of cavities 506 or blisters. The sheet 610 can formed as part of the sealing layer 504 discussed above or be a separate layer that is overlaid thereon. The authenticator indicia 600A can also be printed on, etched into, blazed into, or burned onto (using a laser or heat source) the sealing layer 504 or alternatively a portion of the sealing layer 504. In a preferred embodiment the authenticator indicia 610 are disposed over or within an observable surface that is directly or at least partially disposed over the dose of medication that is to be contained in the cavity or blister portion. These authenticator indicia shown in FIG. 6B may also be referred to as an outside authenticator 600A.

Figure 6C:
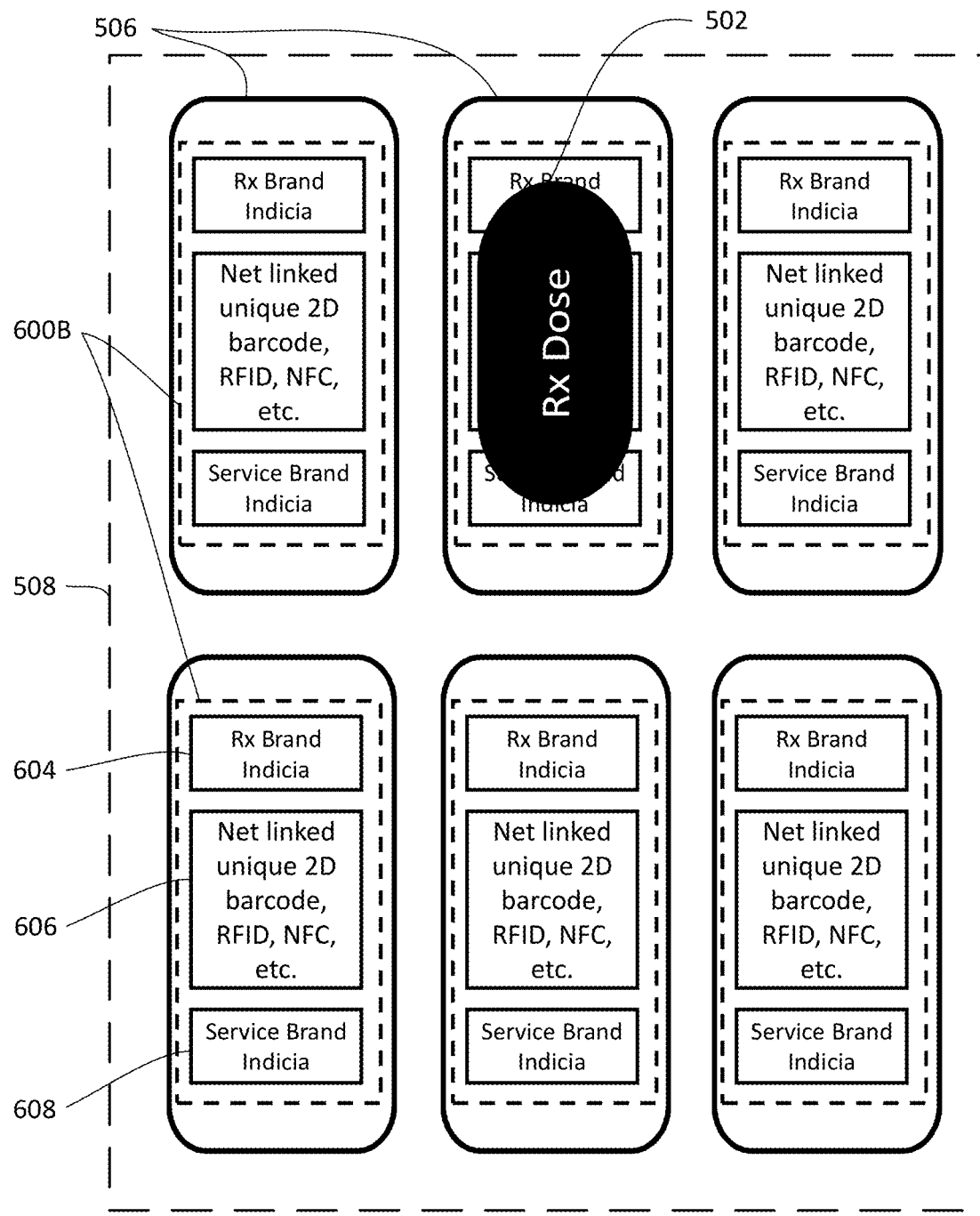

In another configuration, shown in FIG. 6C the authenticator indicia 600B can be disposed within the cavity 506, such as on the inside bottom surface of the cavity 506. As shown, when a dose of medication 502 is placed therein it can cover at least partially a portion of the authenticator from being viewed. Furthermore, when the sealing layer 504 is placed over top the cavity portion the ability to view the authenticator indicia 600B can be completely restricted. In other words, the sealing layer can be non-translucent or non-transparent layer to restrict viewing into the cavity. Alternatively, the outside authenticator 600A can block the view in addition to the dose of medication 502. The cavity or blister portion 506 can also have non-translucent, or non-transparent qualities as well.

In this configuration or location of the authenticator indicia, as shown in FIG. 6C, it can also be referred to as the inside authenticator 600B. The outside authenticator 600A and inside authenticator 600B each have their own unique identification number encoded therein. These unique identification numbers (one from 600A and one from 600B), as will be discussed in more detail below, can be associated with the single dose of medication 502 and used for authenticating the dose of medication.

FIGS. 6D.1-6D.2 illustrate yet another location or configuration of an authenticator indicia 600C, which is placing the Authenticator Indicia onto the dose of medication 502. The two figures shown use different shapes of doses of medication 502 to illustrate the Authenticator Indicia 600C can be adapted to various shapes and surfaces accordingly. Authenticator Indicia 600C can also be referred to as an on-dose authenticator. As disclosed so far, there can be at least a first, second and third versions of authenticators each having their own unique identification number and other indicia associated therewith. Again, additional authenticators in additional configurations and locations are possible, thus the examples are not meant to be exhaustive, but rather principles of what can be.

It should be noted that in one embodiment only a single outside authenticator is used for authenticating a dose of medication. In another embodiment only the inside authenticator is used for authenticating a dose of medication and in yet another embodiment both the outside and inside authenticators are used to authenticate the dose of medication. In yet another embodiment, the outside authenticator and the on-dose authenticator can be used. Alternatively, a first and second authenticator can be used or even a first, second and third authenticator can be used.

FIGS. 6E.1-6E.2 illustrate utilizing an authenticator indicia 600D with a dose container 620 having a cavity or pocket 622 configured to hold a plurality of medications 502 and/or vitamins/supplements 503. FIG. 6E.2 shows authenticator indicia 600D on the outside of the dose container 620, but similar to some of the embodiments previously described an inside authenticator could be disposed on the inside of the dose container 620 for example in the cavity or pocket 622 that is only viewable upon opening the dose container 620 (though not shown). Also, as described previously one or more medications 502 or vitamins/supplements 503 could have an on-pill authenticator indicia. As noted above the dose container 620 could be a blister pack, or a pill pack, or other type of dose container that has a cavity configured to hold multiple pills. In the version of a pill pack, each pill pack can be connected along and edge and formed into a roll or tape, which is then stored in another housing or container that dispenses each pack (containing a plurality of pills) one at time, that can be separated from the rest of the roll or tape. An authenticator Indicia can be placed on the container or housing where the tape or roll of pill packs is stored.

Figure 7:
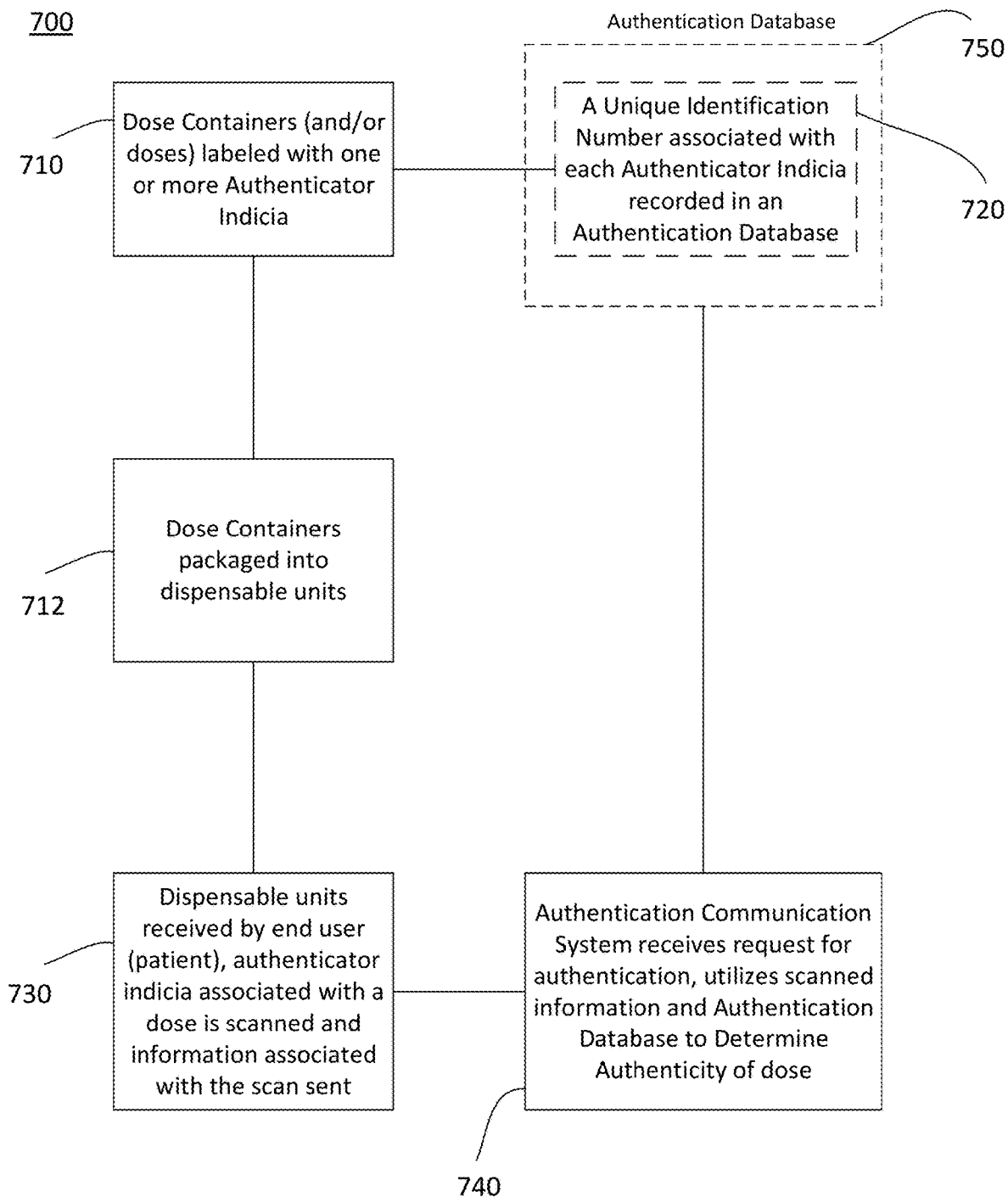
FIG. 7 illustrates a flowchart of a method of authenticating a dose of medicine.

FIG. 7 illustrates a flowchart of a method 700 of preparing 710, packaging 712, dispensing 730, and initiating 740 the authentication process for doses of medicine. In step 710 dose containers are labeled or otherwise provided with authenticator indicia, such as 600, described above. A unique identification number that is associated with each authenticator indicia can be recorded in step 730 in an authentication database 750. The dose containers can then be packaged into dispensable units in step 712. Once the dispensable units are distributed, the end user, such as patient who was prescribed the medication by a medical professional, can scan the authenticator indicia using the smartphone computerized medical device and send scanned information via a networked connection to the authentication communication system in step 730. The scanned authenticator indicia and request for authentication can be received by the authentication communication system in step 740. The authentication communication system can then use the scanned authenticator indicia and information associated with the request, as well as the authentication database to determine the authenticity of the dose of medication. For purposes of this application, it should be understood that a medical professional can include medical doctors, nurses, pharmacists, nutritionists, dieticians, physician's assistants, dentists, optometrists, physical/occupational/addiction therapists, psychiatrists, and others that would be within this scope in view of these examples. It will be understood that these steps in this embodiment, and related embodiments, are carried out using the computerized system discussed above.

Figure 8A:
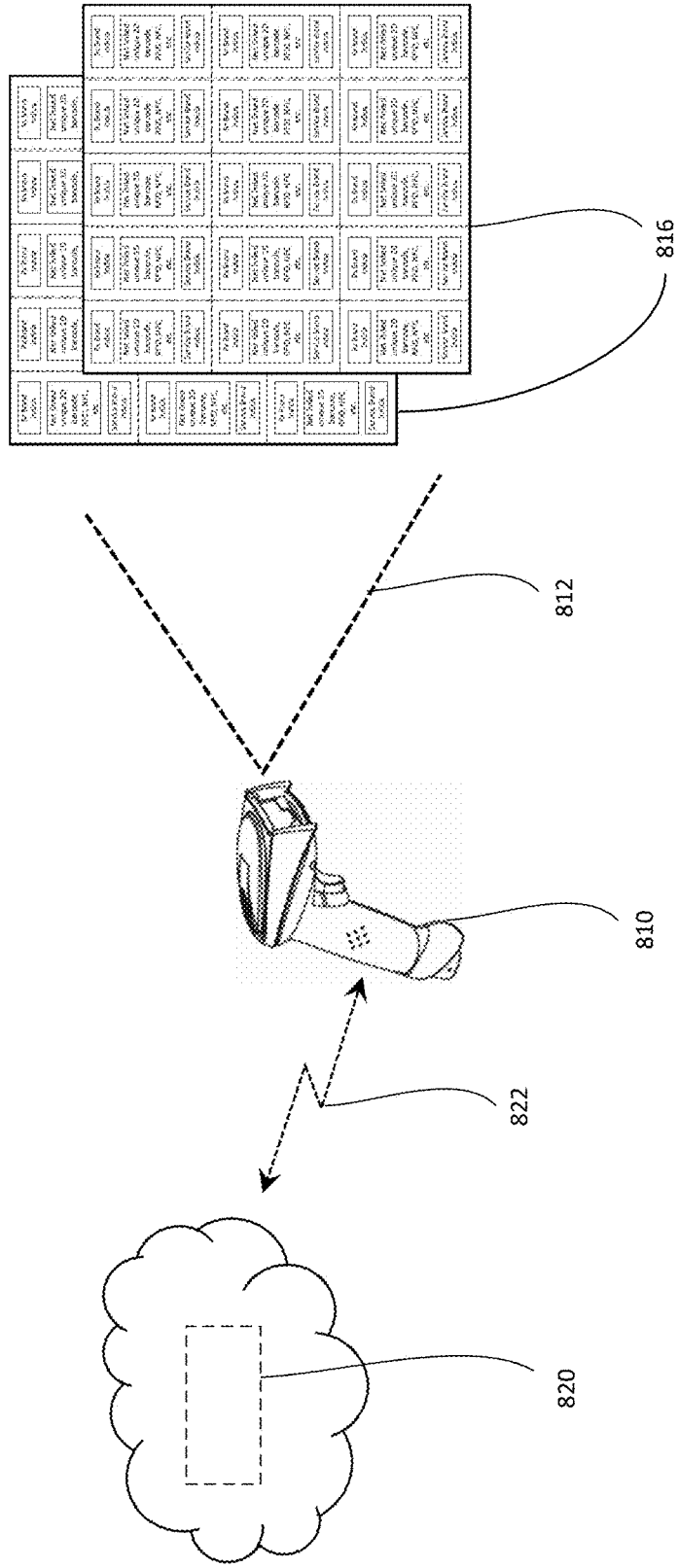
FIGS. 8A-C are various diagrams illustrating steps and systems associated with method and system for authenticating a dose of medicine.
Figure 8B:
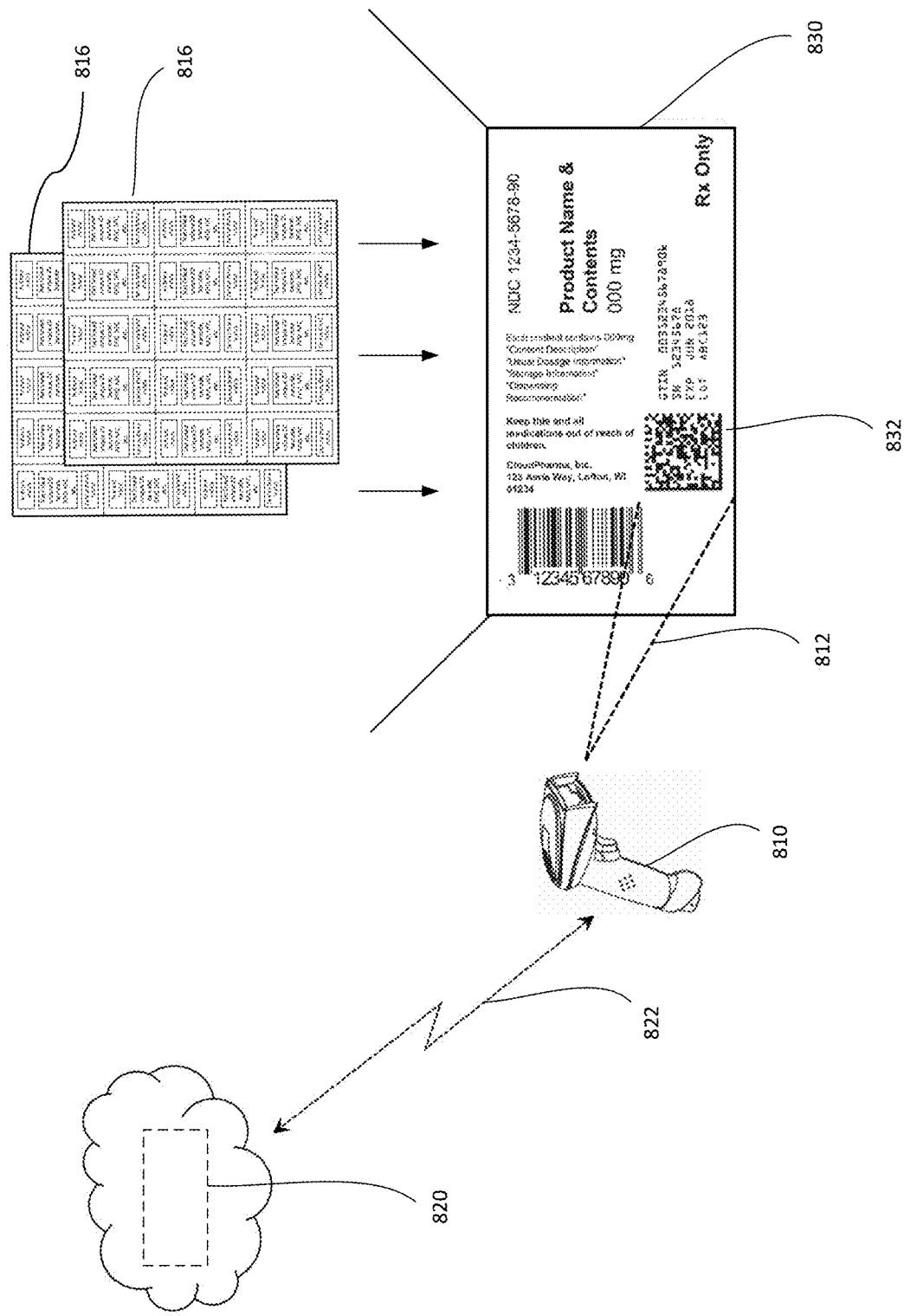
Figure 8C:
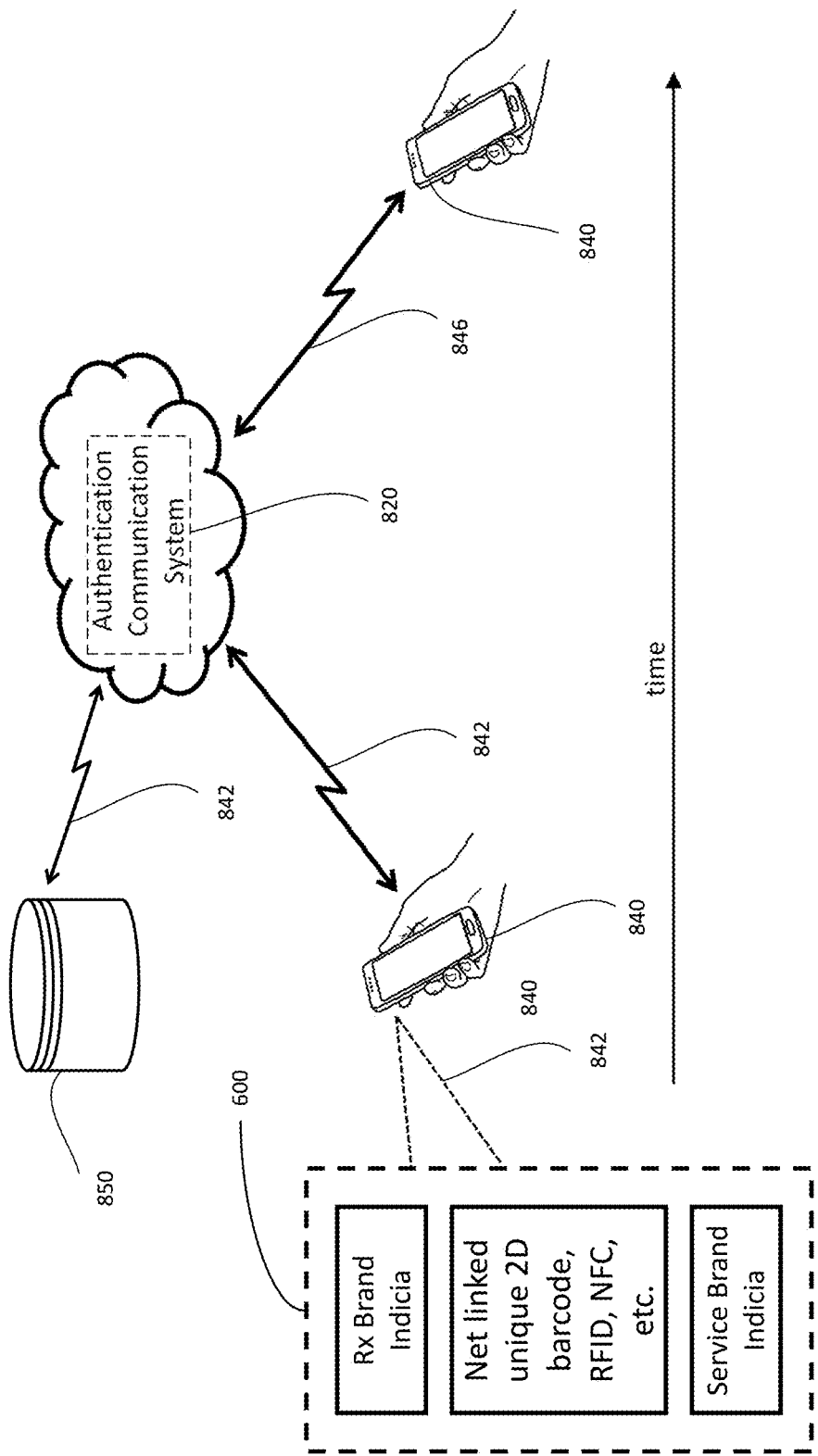

FIGS. 8A-C illustrate various structural and system components for implementing the method shown and described in FIG. 7 and above. FIG. 8A illustrates utilizing a scanning tool 810 to scan all of the external indicia of the authenticable doses 816. The scanned information can then be transmitted via a network 822 to the authenticator communication system 820, which can be hosted in the cloud. It should be noted that scanning tool 810 can be comprised of a variety of types including, 2D barcode scanning device, imaging camera on a smartphone, tablet or other computing device, laser scanner, printer scanner, or other device utilized to detect a visual authenticator indicator. In the embodiments where the authenticator indicia have a radio or electromagnetic component, an appropriate RFID, NFC, or other radio transceiving device can be used to account for the non-visual indicia components. As noted above, the information scanned from the authenticator indicia, such as the unique identification number can be transmitted by the scanning tool or a computing device associated with the scanning to the authenticator communication system 820 for authentication analysis and determination. Additionally, the scanning tool can transmit location-based information derived from GPS information, IP addresses, registries, cellular network or other location-based technologies along with the unique identification number. Time, date and user information can be transmitted. Information about product, lot and purchase order can also be transmitted.

FIG. 8B shows that DSCSA GS1 datamatrix 832 which manufactures can place on the unit of sale to pharmacy carton 830 can be linked to the external indicia of all of the authenticable doses 816 placed in that carton 830. This link can be transmitted to the authenticator communication system 820.

FIG. 8C illustrates an end user utilizing a smartphone 840 having a camera or other scanning tool to scan an authenticator indicia 600 associated with a dose of medication. The scanned information including the unique identification number and location information are transmitted 842 to the authentication communication system 820, which can then utilize the unique identification number along with stored information in the authentication database to determine the authenticity of the dose of medication. As previously noted, location information, time or date information and user information can also be utilized as part of authenticating determination process. Once an authentication determination has been realized system 820 can then transmit 846 authenticity information to a user portal accessible by smartphone 840. Additionally, and in some implementations of the system, system 820 can request access to a user profile, or the user profile associated with the end user that is prescribed the dose of medication, prior to transmitting authentication determination information.

Figure 9A:
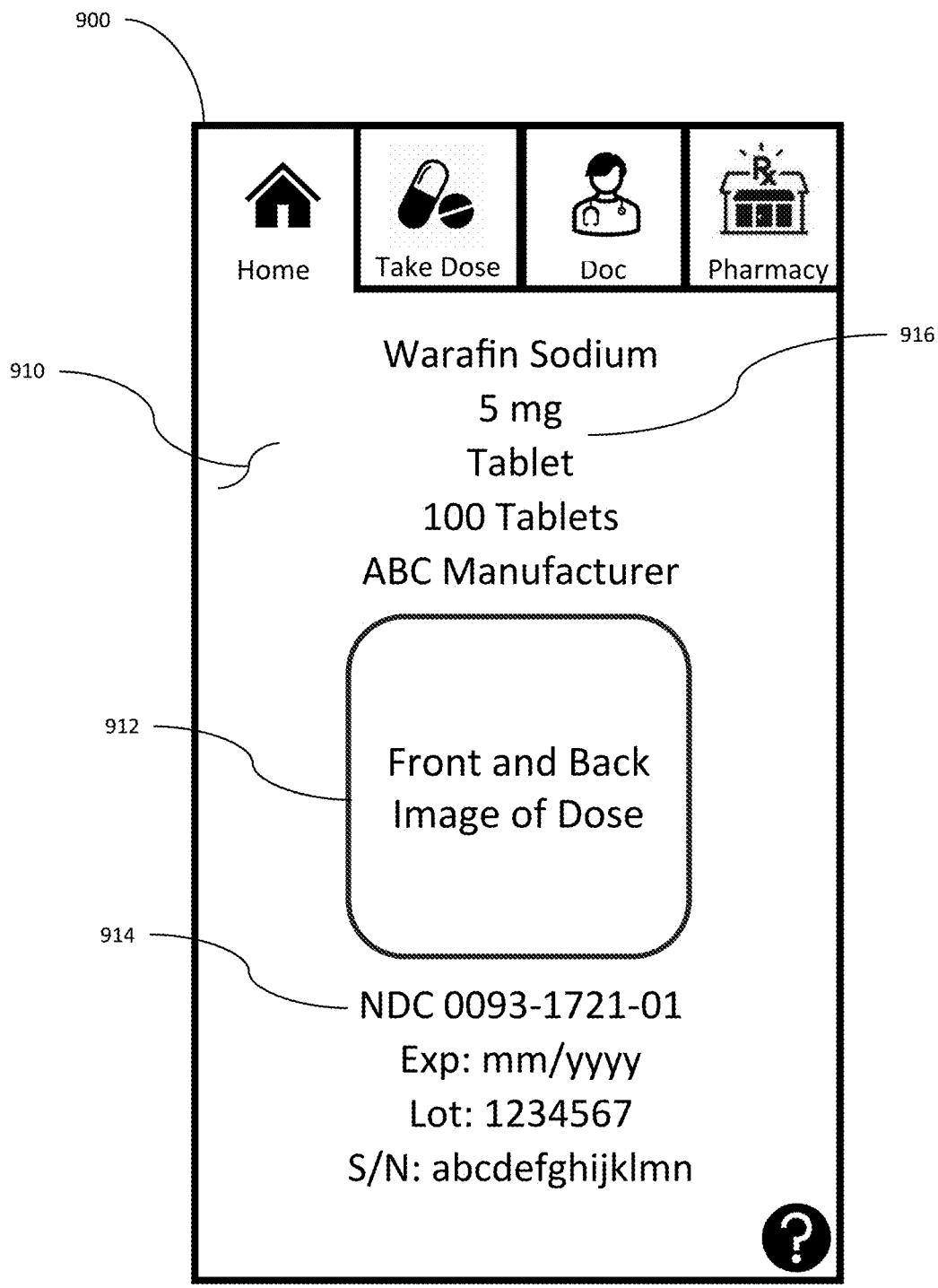
FIGS. 9A-C illustrates various screenshots of a medical device interactions with the patient as they interact with a dose of medicine and establish a secure communication between patient and doctor.
Figure 9B:
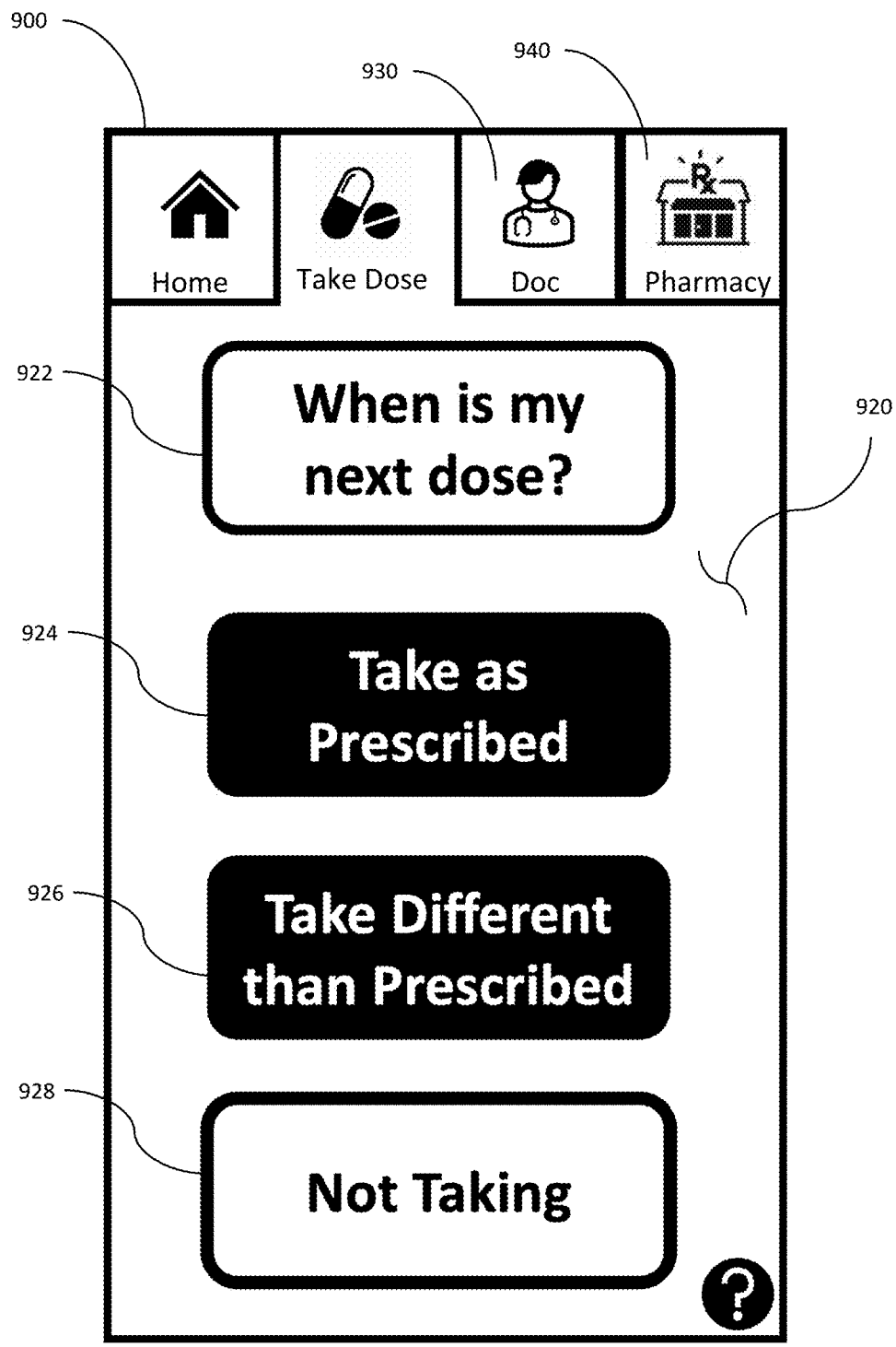
Figure 9C:
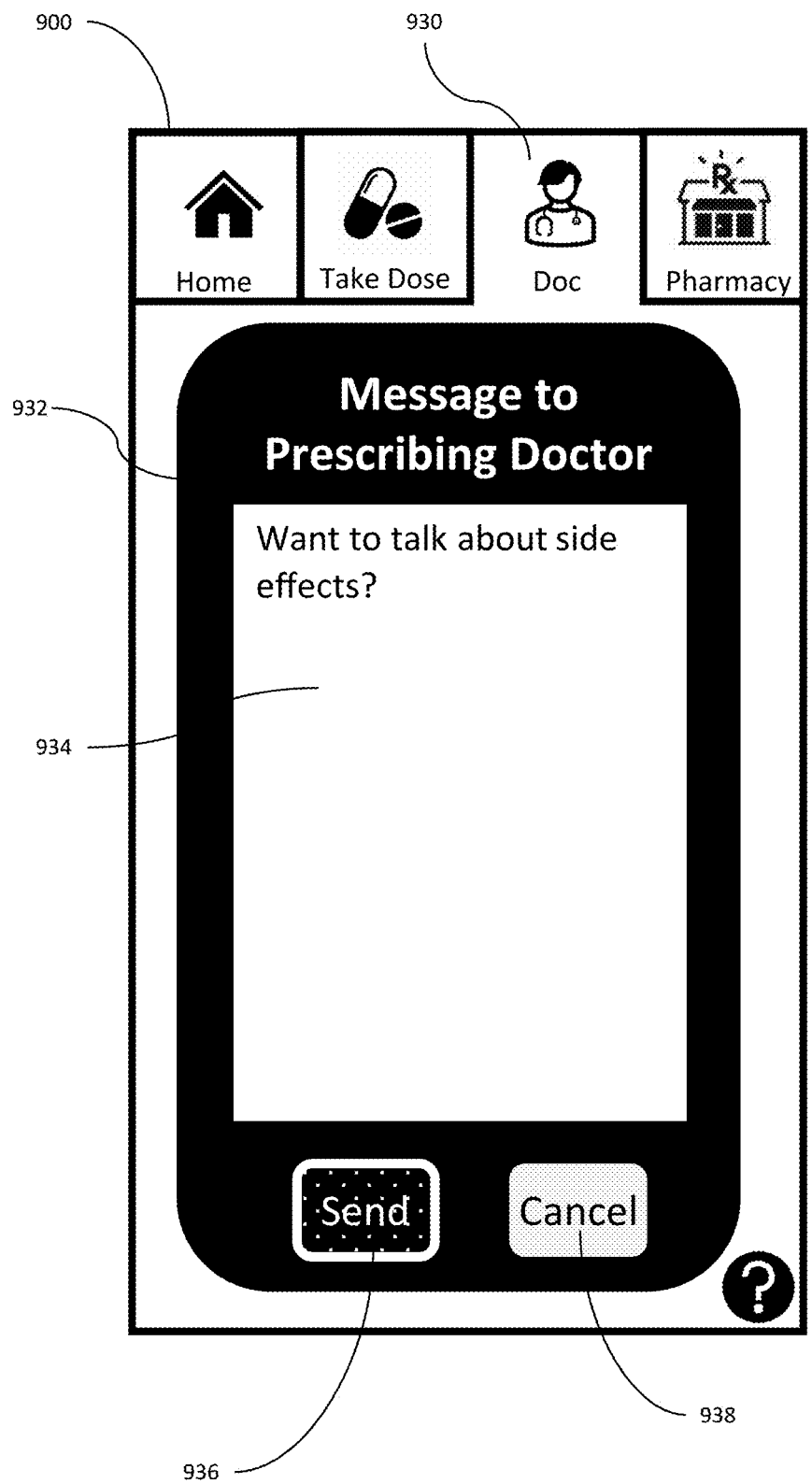

FIGS. 9A-C illustrate a user portal 900 for accessing and utilizing the computerized medical device for medications dispensed to patients. As shown in FIG. 9A, user portal 900 has can have a variety of interfaces, such as interface 910, which provides basic information about the medication. Another interface 920 shown in FIG. 9B can be utilized to initiate action relative to taking the next dose of medicine. Interface 920 can include transmitted information through the medical device regarding the appropriate time to take the next dose, history of previous doses taken, reminders and alerts related to taking the next dose, and tracking adherence or non-adherence to the prescribed medical script. Some of these features are shown in sections 922, 924, 926 and 928 by way of example and are not limiting. From this interface, other interfaces can be selected to initiate communication with a medical provider 930 or enabling and optionally initiating a prescription refill 940. This information can be stored in a database, such as a user profile database, that is accessible by the medical device and end user.

The user interface presented on the computerized medical device (in typical embodiments, a smartphone or tablet) is operable to contain all of its features within the continuous user interface of the system. Importantly, in many embodiments, a user need not navigate out of the user interface of the system to access other portions of the systems functionality. For example, camera activation and recording may be performed through the user interface, rather than having to use the phones standard camera recording operations. Similarly, data access of user information can be performed through the user interface, rather than having to access a third party system. Further, the attestation functionality may be generated and presented through the user interface, again without requiring the user navigate away into other systems, apps, or web pages. The other features disclosed herein similarly are integrated into the system's user interface. As is known in the art, there is a problem with computerized operations where users navigate away from a web page, app, or other user interface, never to return. This problem is particularly present in the present instance where the goal is to increase adherence and persistence in a medical regimen, where the slightest distraction can meaningfully reduce both adherence and persistence. Therefore, the present system solves this problem of both the computer arts and the medical treatment arts by providing a consistent user interface which provides the functionality in a single system, without requiring navigation away.

Interface 930 shown in FIG. 9C can be utilized to invite and communicate with third parties like medical providers or authorized support persons. Section 932 provides a messaging portal with a messaging section 934 and means to send 936 the message or cancel/delete 938 the message. These communications can be stored with the user profile information, stored locally on a device accessing the portal 900, or deleted instantly upon closing the portal.

As mentioned, the methods, systems and structure described assist with the creating a reliable record of consumption of doses of medication, as well as generating evidence of dispensed medication authenticity and its consumption.

It should be understood that the systems described above may provide multiple ones of any or each of those components and these components may be provided on either a standalone machine or, in some embodiments, on multiple machines in a distributed system. The phrases 'in one embodiment,' 'in another embodiment,' and the like, generally mean that the particular feature, structure, step, or characteristic following the phrase is included in at least one embodiment of the present disclosure and may be included in more than one embodiment of the present disclosure. Such phrases may, but do not necessarily, refer to the same embodiment.

The techniques described above may be implemented as a method, apparatus, or article of manufacture using programming and/or engineering techniques to produce software, firmware, hardware, or any combination thereof. The techniques described herein may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices. As indicated above, software (also referred to herein as components, modules, programs, program code, and applications) may include virtual machines and virtualized software.

Any of the functions disclosed herein may be implemented using means for performing those functions. Such means include, but are not limited to, any of the components disclosed herein.

Each computer program within the scope of the claims below may be implemented in any programming language, such as assembly language, machine language, a high-level procedural programming language, or an object-oriented programming language. The programming language may, for example, be LISP, PROLOG, PERL, C, C++, C#, JAVA, PYTHON, HTMLS or any compiled or interpreted programming language.

Each such computer program may be implemented in a computer program product tangibly embodied in a machine-readable storage device for execution by a computer processor. Method steps of the invention may be performed by a computer processor executing computer program instructions tangibly embodied on a non-transitory computer-readable medium to perform functions of the invention by operating on input and generating output. Cookies, operating systems, and other information may also be stored on non-transitory computer-readable medium. Suitable processors include, by way of example, both general and special purpose microprocessors. Generally, the processor receives instructions and data from a read-only memory and/or a random-access memory. Storage devices suitable for tangibly embodying computer program instructions include, for example, all forms of computer-readable devices, firmware, programmable logic, hardware (e.g., integrated circuit chip; electronic devices; a computer-readable non-volatile storage unit; non-volatile memory, such as semiconductor memory devices, including EPROM, EEPROM, and flash memory devices; magnetic disks such as internal hard disks and removable disks; magneto-optical disks; and CD-ROMs). Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data from a second computer providing access to the programs via a network transmission line, wireless transmission media, signals propagating through space, radio waves, infrared signals, etc.

While several variations of the present disclosure have been illustrated by way of example in preferred or particular embodiments, it is apparent that further embodiments could be developed within the spirit and scope of the present disclosure, or the inventive concept thereof. However, it is to be expressly understood that such modifications and adaptations are within the spirit and scope of the present disclosure, and are inclusive, but not limited to the following appended claims as set forth.

What is claimed is:

1. A computerized medical device for treating a patient with a prescription dispensed to the patient, the computerized medical device operable to:
receive medication prescription information from a patient through a user input interface of the computerized medical device, the medication prescription information comprising a patient user ID, a drug name, and directions for use;
receive a notice of medication consumption, including a first date and time that the patient consumed a dispensed medication, provided by a clock of the computerized medical device, in either of: via a prompt on a display of the computerized medical device and a receipt of an input to the user input interface, or from the dispensed medication itself, its packaging, its container, or its label, by scanning, using a camera of the computerized medical device, of a unique internet addressable 2D barcode on the dispensed medication, its package, its container, or its label, by scanning or inputting the dispensed package DSCSA GS1 Data Matrix, GTIN, serial number, expiration date, lot number, UPC code, or any alphanumeric number or code, or by scanning, using image recognition, the dispensed medication, its package, its container, or its label, or receive an additional notice of medication consumption; wherein the additional notice of medication consumption includes a first attestation from the patient, indicating that this is the dispensed medication or an second attestation as to the first date and time that the patient consumed the dispensed medication;
create a digital record of the medication prescription information and the notice of medication consumption, the digital record being a data file saved on a memory accessible to the computerized medical device; and
provide an output from the computerized medical device comprising suggestions for the patient regarding the dispensed medication, wherein the suggestions are based on the medication prescription information, the patient notices of medication consumption, and a current date and time.

2. The medical device for treating a patient with a prescription dispensed to the patient of claim 1, wherein the computerized medical device is operable to receive medication prescription information; wherein the medication prescription information includes at least one of patient identification, prescriber identification, drug name, drug strength, dosage form, quantity prescribed, directions for use, date dispensed, quantity dispensed, dispensing pharmacy, dispensing pharmacy prescription number, or dispensing pharmacy phone number.

3. The medical device for treating a patient with a prescription dispensed to the patient of claim 1, wherein the computerized medical device is in communication with a network and operable to provide secure real-time or delayed communication with a server about the medication prescription information and the notice of medication consumption.

4. The medical device for treating a patient with a prescription dispensed to the patient of claim 1, wherein the computerized medical device is in communication with a network and operable to request and receive the medication prescription information for a patient from servers, by entering the unique pharmacy phone number and prescription number using the user input interface of the computerized medical device, or by scanning, using the camera of the computerized medical device.

5. The medical device for treating a patient with a prescription dispensed to the patient of claim 1, wherein the computerized medical device operable to enable a prescription refill process based on calculations from the medical device, that it's time for an automatic refill, based on input by the patient to the computerized medical device, or by scanning using the camera of the computerized medical device, through a networked communication with a pharmacy.

6. The medical device for treating a patient with a prescription dispensed to the patient of claim 1, wherein evidence that the dispensed medication was is able to be received from the patient from the dispensed medication itself, its packaging, its container, or its label, by the computerized medical device, individually or in combination, by:
  operating the computerized medical device to take a photo of the dispensed medication, its packaging, its container, or its label using the camera;
  scanning, using the camera of the computerized medical device or entering, using the user input interface of the computerized medical device, the pharmacy phone number or prescription number, or both the pharmacy phone number and prescription number;
  scanning, using the camera of the computerized medical device, of a 2D barcode on the dispensed medication, its package, its container, or the label;
  scanning, using the camera of the computerized medical device, of the dispensed package DSCSA GS1 Data Matrix or UPC code, or
  entering, using the user input interface of the computerized medical device, the dispensed package GTIN, serial number, expiration date, lot number, or UPC code, individually or in combination;
  scanning, using the camera of the computerized medical device, using image recognition, of the dispensed medication, its container, its package, or the label;
  scanning, using the camera of the computerized medical device, a dose to confirm single factor authentication of the dispensed medication; or
  scanning, using the camera of the computerized medical device, a dose to confirm multi-factor authentication of the dispensed medication.

7. The medical device for treating a patient with a prescription dispensed to the patient of claim 6, wherein evidence that the dispensed medication was dispensed to this patient is able to be generated from a single-factor authenticatable dose comprising the steps of:
  providing an outside or inside dose authenticator on or in a blister pack or sealed enclosure containing at least one dose of the dispensed medication;
  associating the outside or inside dose authenticator of the blister pack or sealed enclosure with each of the at least one dose of the dispensed medication in a database;
  associating in a database the outside or inside dose authenticator with other dose authenticators within the same unit of sale, defined as within the same DSCSA serial number;
  scanning the outside or inside dose authenticator, using the camera of the computerized medical device;
  providing an authenticating communication system configured to receive scanned information from the outside or inside dose authenticator; and
  determining whether the dose of the dispensed medication is authentic based on available data.

8. The medical device for treating a patient with a prescription dispensed to the patient of claim 6, wherein evidence that the dispensed medication was dispensed to this patient is able to be generated by a multi-factor authenticatable dose comprising the steps of:
  providing an outside authenticator on a blister pack or sealed enclosure containing at least one dose of the dispensed medication;
  providing an inside authenticator located inside the blister pack or sealed enclosure, wherein the inside authenticator is not completely viewable until the blister pack or sealed enclosure is opened, and wherein the inside authenticator may be on the dispensed medication itself via inscription, printing, molding, or attachment;
  associating the outside and inside authenticators of each blister pack or sealed enclosure with each dose of the dispensed medication in a database;
  associating in a database a dose authenticator with other dose authenticators within the same unit of sale, defined as within the same DSCSA serial number;
  scanning the outside and inside authenticators, using the camera of the computerized medical device;
  providing an authenticating communication system configured to receive scanned information from the outside and inside authenticators; and
  determining whether the at least one dose of the dispensed medication is authentic based on available data.

9. The medical device for treating a patient with a prescription dispensed to the patient of claim 4, wherein other medications, vitamins, or nutritional supplements taken at the same time are also able to be placed in the blister pack or sealed enclosure.

10. The medical device for treating patients with a prescription dispensed to the patient of claim 6, wherein the device is operable to create a digital record of evidence that the dispensed medication, the digital record being a data file saved on a memory accessible to the computerized medical device.

11. The medical device for treating a patient with a prescription dispensed to the patient of claim 1, wherein evidence of notices of consumption is able to be received from the patient by enabling patients to create a video record of their consumption using one or both of a front camera and a back camera individually or simultaneously wherein the video record starts at a beginning of the process and records continuously through to final completion, and create a digital record of the evidence, the digital record being a data file saved on a memory accessible to the computerized medical device.

12. The medical device for treating a patient with a prescription dispensed to the patient of claim 1, the computerized medical device operable to provide automatic reminders via a prompt on a display of the computerized medical device for the patient to take an appropriate dose at an appropriate time, to warn the patient on a display of the computerized medical device in response to scanning of an incorrect type of medication, or of a counterfeit medication, or of a dose of medication that has been previously consumed by the patient, or to warn the patient on the display of the computerized medical device in response to an incorrect time for medical consumption.

13. The medical device for treating a patient with a prescription dispensed to the patient of claim 1, the computerized medical device operable to receive an input from the patient, via a prompt on a display of the computerized medical device and a receipt of an input to the user input interface wherein the patient is provided an option to automatically share drug consumption information with caregivers, family, friends, researchers, or healthcare providers via networks.

14. The medical device for treating a patient with a prescription dispensed to the patient of claim 1, the computerized medical device operable to:
  provide individual or team games for patients to play on the computerized medical device which maintain or improve patience persistence and adherence;
  notify, track and deliver rewards, or financial incentives to patients for maintaining or improving their persistence and adherence; the delivery of rewards and financial incentives being initiated via a prompt on a display of the computerized medical device and a receipt of an input to the user input interface, which is able to be relayed through networks by the computerized medical device;

enable a patient or population of patients an option to participate in medical research for conditions treated with prescription drugs; or create or link the patient to a social network, which enables the patient to communicate through the computerized medical device with other patients having similar conditions, including those with similar or different medication treatments.

15. The medical device for treating a patient with a prescription dispensed to the patient of claim 1, wherein the computerized medical device is operable to: retrieve a historical record of the medication prescription information and the notice of medication consumption corresponding to the patient from a memory accessible to the computerized medical device.

16. The medical device for treating a patient with a prescription dispensed to the patient of claim 8, wherein other medications, vitamins, or nutritional supplements taken at the same time are also able to be placed in the blister pack or sealed enclosure.

17. A computerized medical device for treating a patient with a prescription dispensed to the patient, the computerized medical device operable to:

receive medication prescription information from a patient through a user input interface of the computerized medical device, the medication prescription information comprising a patient user ID, a drug name, and directions for use;

receive a notice of medication consumption, including the date and time that the patient consumed the dispensed medication, provided by a clock of the computerized medical device, via a prompt on a display of the computerized medical device and a receipt of an input to the user input interface or by scanning, using a camera of the computerized medical device, of a unique internet addressable 2D barcode on the drug its package, or the label, by scanning the dispensed package DSCSA GS1 Data Matrix, or by scanning, using image recognition, of the container, package, label, or medication;

gather evidence that the dispensed medication consumed was authentic medication dispensed to the patient from the dispensed medication itself, its packaging or its label;

create a digital record of the medication prescription information, the notice of medication consumption, and gathered evidence, the digital record being a data file saved on a memory accessible to the computerized medical device;

retrieve a historical record of the medication prescription information, the notice of medication consumption, and gathered evidence corresponding to the patient from a memory accessible to the computerized medical device;

provide an output from the computerized medical device comprising suggestions for the patient regarding the prescription, wherein the suggestions are based on the medication prescription information, the patient notices of medication consumption, and a current date and time;

wherein the documentation communication system is comprised of one or more processors associated with a set of computer executable instructions in memory configured to receive information and data associated with each dose, its prescription, its notices of consumption together with supporting evidence, if any, utilize the database comprising stored information about each dose, its prescription, dispensing, and its notices of consumption, together with supporting evidence, if any, generate and store user profile information associated with a plurality of end users in a user profile database, and create secure connections between end users and medical professionals or support persons.

18. The medical device for treating a patient with a prescription dispensed to the patient of claim 17, wherein evidence that the prescription was dispensed to the patient is able to be received from the patient by the computerized medical device, individually or in combination, by operating the computerized medical device to take a photo of the dispensed medication, its packaging, its container, or its label using the camera;

scanning, using the camera of the computerized medical device or entering, using the user input interface of the computerized medical device, a pharmacy phone number or prescription number;

scanning, using the camera of the computerized medical device, of a unique internet addressable 2D barcode on the dispensed medication, its package, its container, or the label;

scanning, using the camera of the computerized medical device, of the dispensed package DSCSA GS1 Data Matrix or UPC code;

entering, using the user input interface of the computerized medical device, the dispensed package GTIN, serial number, expiration date, lot number, or UPC code, individually or in combination;

scanning, using the camera of the computerized medical device, using image recognition, of the prescription, its container, its package, or the label;

scanning, using the camera of the computerized medical device, a dose to confirm single factor authentication of the dispensed medication or multi-factor authentication of the prescription.

19. The medical device for treating a patient with a prescription dispensed to the patient of claim 17, wherein evidence of the notice of consumption is able to be received from the patient by enabling patients to create a video record of their consumption using one or both of a front camera and a back camera individually or simultaneously, which recording is able to start at a beginning of the process and record continuously through to final completion, and create a digital record of the evidence, the digital record being a data file saved on a memory accessible to the computerized medical device.

* * * * *